US006455255B1

(12) United States Patent
Birkenmeyer et al.

(10) Patent No.: US 6,455,255 B1
(45) Date of Patent: Sep. 24, 2002

(54) METHOD OF PERFORMING SUBTRACTIVE HYBRIDIZATION USING RDA

(75) Inventors: Larry G. Birkenmeyer, Chicago, IL (US); Thomas P. Leary; A. Scott Muerhoff, both of Kenosha, WI (US); Suresh M. Desai, Libertyville; Isa K. Mushahwar, Grayslake, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/631,349

(22) Filed: Aug. 2, 2000

(51) Int. Cl.[7] ............................ C12Q 1/68; C12P 19/34; C12M 1/34; C07H 21/02; C07H 21/04

(52) U.S. Cl. .............................. 435/6; 435/6; 435/91.1; 435/91.2; 435/285.1; 435/287.2; 536/22.1; 536/23.1; 536/24.3; 536/24.31; 536/24.32; 536/24.33

(58) Field of Search ................................ 435/5, 6, 91.1, 435/91.2, 285.1, 287.2; 536/22.1, 23.1, 24.3, 24.31, 24.32, 24.33

(56) References Cited

U.S. PATENT DOCUMENTS

| | | | |
|---|---|---|---|
| 4,683,195 A | | 7/1987 | Mullis et al. |
| 5,958,738 A | | 9/1999 | Lindemann et al. |
| 6,159,713 A | * | 12/2000 | Wigler et al. ............... 435/91.2 |
| 6,235,503 B1 | | 5/2001 | Lindenmann et al. |

FOREIGN PATENT DOCUMENTS

WO    WO-9923256 A1 * 5/1999

OTHER PUBLICATIONS

Ermolaeva, et al., *Genetic Analysis: Biomolecular Engineering*, Subtractive Hybridization, a Technique for Extraction of DNA Sequences Distinguishing Two Closely Related Genomes: Critical Analysis, 13:49–58 (1996).

Hubank, et al., *Nucleic Acids Research*, Identifying Differences in mRNA Expression by Representational Difference Analysis of cDNA, 22:5640–5648 (1994).

Saiki, et al., *Science*, Enzymatic Amplification of β–Globin Genomic Sequences and Restriction Site Analysis for Diagnosis of Sickle Cell Anemia, 230:1350–1354 (1985).

Simons, et al., *Proc. Natl. Acad. Sci. USA*, Identification of Two Flavivirus–Like Genomes in the GB Hepatitis Agent, 92:3401–3405 (1995).

Ushijima, at al., *Proc. Natl. Acad. Sci. USA*, Establishment of Methylation–Sensitive–Representational Difference Analysis and Isolation of Hypo– and Hypermethylated Genomic Fragments in Mouse Liver Tumors, 94:2284–2289 (1997).

* cited by examiner

*Primary Examiner*—Jeffrey Siew
(74) *Attorney, Agent, or Firm*—Cheryl L. Becker; Dianne Casuto

(57) ABSTRACT

The subject invention relates to improvements in nucleic acid isolation, and more particularly, relates to modifications to the subtractive hybridization method and to reagents such as oligonucleotides that are useful when performing the method.

8 Claims, 5 Drawing Sheets

R-Bam 24   5' AGCACTCTCCAGCCTCTCACCGAG 3' (SEQ. ID No: 1)
           3' TCGTGAGAGGTCGGAGAGTGGCTCCTAGnnnnCTAGGAGCCACTCTCGACCTCTCACGA 5'

5' AGCACTCTCCAGCCTCTCACCGAGGATCnnnnGATCCTCGGTGAGAGGCTGGAGAGTGCT 3' (SEQ. ID No: 19)
R-Bam 24   3'                         GAGCCACTCTCCGACCTCTCACGA 5'

FIG.1A

5' AGCCTCTCACCGAGGATCN 3' (SEQ. ID No: 20)
R-Bam 19N  3' TCGTGAGAGGTCGGAGAGTGGCTCCTAGnnnnCTAGGAGCCACTCTCCGACCTCTCACGA 5'

5' AGCACTCTCCAGCCTCTCACCGAGGATCnnnnGATCCTCGGTGAGAGGCTGGAGAGTGCT 3' (SEQ. ID No: 21)
R-Bam 19N  3'                         NCTAGGAGCCACTCTCCGA 5'

FIG.1B

SEQUENCE LISTING

<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Primer R-Bam 24

<400> SEQUENCE: 1
agcactctcc agcctctcac cgag        24

<210> SEQ ID NO 2
<211> LENGTH: 12
<212> TYPE: DNA
<213> ORGANISM: Artificial Sequence
<220> FEATURE:
<223> OTHER INFORMATION: Primer R-Bam 12

<400> SEQUENCE: 2
gatcctcggt ga        12

<210> SEQ ID NO 3
<211> LENGTH: 19
<212> TYPE: DNA
<213> ORGANISM: Artificial Sequence
<220> FEATURE:
<223> OTHER INFORMATION: Primer R-Bam 19C

<400> SEQUENCE: 3
agcctctcac cgaggatcc        19

```
<210> SEQ ID NO 4
<211> LENGTH: 19
<212> TYPE: DNA
<213> ORGANISM: Artificial Sequence
<220> FEATURE:
<223> OTHER INFORMATION: Primer R-Bam 19G

<400> SEQUENCE: 4
agcctctcac cgaggatcg                                                     19

<210> SEQ ID NO 5
<211> LENGTH: 24
<212> TYPE: DNA
<213> ORGANISM: Artificial Sequence
<220> FEATURE:
<223> OTHER INFORMATION: Primer J-Bam 24

<400> SEQUENCE: 5
accgacgtcg actatccatg aacg                                               24

<210> SEQ ID NO 6
<211> LENGTH: 12
<212> TYPE: DNA
<213> ORGANISM: Artificial Sequence
<220> FEATURE:
<223> OTHER INFORMATION: Primer J-Bam 12

<400> SEQUENCE: 6
gatccgttca tg                                                            12

<210> SEQ ID NO 7
<211> LENGTH: 24
<212> TYPE: DNA
<213> ORGANISM: Artificial Sequence
<220> FEATURE:
<223> OTHER INFORMATION: Primer N-Bam 24

<400> SEQUENCE: 7
aggcaactgt gctatccgag ggag                                               24

<210> SEQ ID NO 8
<211> LENGTH: 12
<212> TYPE: DNA
<213> ORGANISM: Artificial Sequence
<220> FEATURE:
<223> OTHER INFORMATION: Primer N-Bam

<400> SEQUENCE: 8
gatcctccct cg                                                            12

<210> SEQ ID NO 9
<211> LENGTH: 24
<212> TYPE: DNA
<213> ORGANISM: Artificial Sequence
<220> FEATURE:
<223> OTHER INFORMATION: Primer F-Bam 24

<400> SEQUENCE: 9
accgctactg cactccctcg acag                                               24

<210> SEQ ID NO 10
<211> LENGTH: 12
<212> TYPE: DNA
<213> ORGANISM: Artificial Sequence
<220> FEATURE:
<223> OTHER INFORMATION: Primer F-Bam
```

```
<400> SEQUENCE: 10
gatcctgtcg ag                                                    12

<210> SEQ ID NO 11
<211> LENGTH: 24
<212> TYPE: DNA
<213> ORGANISM: Artificial Sequence
<220> FEATURE:
<223> OTHER INFORMATION: Primer S-Bam 24

<400> SEQUENCE: 11
agggacctgg acatacgatg actg                                       24

<210> SEQ ID NO 12
<211> LENGTH: 12
<212> TYPE: DNA
<213> ORGANISM: Artificial Sequence
<220> FEATURE:
<223> OTHER INFORMATION: Primer S-Bam

<400> SEQUENCE: 12
gatccagtca tc                                                    12

<210> SEQ ID NO 13
<211> LENGTH: 11
<212> TYPE: DNA
<213> ORGANISM: Artificial Sequence
<220> FEATURE:
<223> OTHER INFORMATION: Linker/Adapter BE1F

<400> SEQUENCE: 13
gatccgaatt c                                                     11

<210> SEQ ID NO 14
<211> LENGTH: 7
<212> TYPE: DNA
<213> ORGANISM: Artificial Sequence
<220> FEATURE:
<223> OTHER INFORMATION: Linker/Adapter BE1R

<400> SEQUENCE: 14 gaattcg                                                           7

<210> SEQ ID NO 15
<211> LENGTH: 12
<212> TYPE: DNA
<213> ORGANISM: Artificial Sequence
<220> FEATURE:
<223> OTHER INFORMATION: Linker/Adapter BE2F

<400> SEQUENCE: 15
gatccggaat tc                                                    12

<210> SEQ ID NO 16
<211> LENGTH: 8
<212> TYPE: DNA
<213> ORGANISM: Artificial Sequence
<220> FEATURE:
<223> OTHER INFORMATION: Linker/Adapter BE2R

<400> SEQUENCE: 16 gaattccg                                                          8

<210> SEQ ID NO 17
<211> LENGTH: 13
```

-continued

```
<212> TYPE: DNA
<213> ORGANISM: Artificial Sequence
<220> FEATURE:
<223> OTHER INFORMATION: Linker/Adapter BE3F

<400> SEQUENCE: 17
gatcgcggaa ttc                                                          13

<210> SEQ ID NO 18
<211> LENGTH: 9
<212> TYPE: DNA
<213> ORGANISM: Artificial Sequence
<220> FEATURE:
<223> OTHER INFORMATION: Linker/Adapter BE3R

<400> SEQUENCE: 18 gaattccgc                                                                9

<210> SEQ ID NO 19
<211> LENGTH: 60
<212> TYPE: DNA
<213> ORGANISM: Artificial Sequence
<220> FEATURE:
<223> OTHER INFORMATION: Primer R-Bam 24
<221> NAME/KEY: misc_feature
<222> LOCATION: (29)...(32)
<223> OTHER INFORMATION: n = a or g or c or t/u, unknown or other at
      positions 29-32

<400> SEQUENCE: 19
agcactctcc agcctctcac cgaggatcnn nngatcctcg gtgagaggct ggagagtgct       60

<210> SEQ ID NO 20
<211> LENGTH: 19
<212> TYPE: DNA
<213> ORGANISM: Artificial Sequence
<220> FEATURE:
<223> OTHER INFORMATION: Primer R-Bam 19N
<221> NAME/KEY: misc_feature
<222> LOCATION: (19)...(19)
<223> OTHER INFORMATION: n = a or g or c or t/u, unknown or other at
      position 19

<400> SEQUENCE: 20
agcctctcac cgaggatcn                                                    19

<210> SEQ ID NO 21
<211> LENGTH: 60
<212> TYPE: DNA
<213> ORGANISM: Artificial Sequence
<220> FEATURE:
<223> OTHER INFORMATION: Primer R-Bam 19N
<221> NAME/KEY: misc_feature
<222> LOCATION: (29)...(32)
<223> OTHER INFORMATION: n = a or g or c or t/u, unknown or other at
      positions 29-32

<400> SEQUENCE: 21
agcactctcc agcctctcac cgaggatcnn nngatcctcg gtgagaggct ggagagtgct       60
```

METHOD OF PERFORMING SUBTRACTIVE HYBRIDIZATION USING RDA

BACKGROUND OF THE INVENTION

1. Technical Field

The subject invention relates to improvements in nucleic acid isolation, and more particularly, relates to modifications to the subtractive hybridization method and to reagents such as oligonucleotides that are useful when performing the method.

2. Background Information

Changes to the presence, level, or sequence of a particular nucleic acid can have a significant effect on the host in which the nucleic acid resides. The identification and isolation of such nucleic acid sequences are essential to their analysis and understanding. To this end, the approaches of genetics, infectivity studies, comparative nucleic acid fingerprinting, and subtractive hybridization have been used.

Subtractive hybridization methods enrich for nucleic acid sequences present in one sample but absent, decreased, or altered in an otherwise identical sample. For a review, see O. D. Ermolaeva et al., *Genetic Anal.: Biomol. Eng.* 13:49–58 (1996). A "target" in such methods is the set of nucleic acid sequences to be enriched, and the "tester and driver" are nearly identical nucleic acid samples that preferably differ from one another only by the presence or absence of the target sequence(s) respectively.

Generally, in subtractive hybridization, driver and tester nucleic acid are extracted from the samples; cDNA then is prepared if the nucleic acid of interest is RNA; driver DNA and tester DNA are fragmented and one or the other is modified to enable subsequent purification; and finally, a mixture of the fragmented DNAs, in which driver is in substantial excess over tester, is heat denatured and complementary single strands are allowed to reanneal. Due to the excess of driver versus tester, a majority of tester sequences held in common with driver will exist as tester/driver hybrids. Species containing sequences common to driver and tester are eliminated by means of the described modification, leaving a tester-only population enriched in target sequences. If further enrichment is required, additional rounds of subtraction are performed. Finally, individual fragments cloned from the subtraction products are screened for target sequences (i.e., those sequences present in tester but absent, or significantly reduced, in driver) (O. D. Ermolaeva et al., supra).

Representational Difference Analysis (RDA), like other recent methods of subtractive hybridization incorporate the polymerase chain reaction (PCR) as an integral part of the procedure (U.S. Pat. No. 4,683,195; Saiki et al., *Science* 230:1350–1354 (1985)). The success of PCR-based subtractive hybridization is partially dependent on the initial amplicon complexity and/or the relative abundance of target sequence within the amplicon. (An amplicon may be defined as the entity comprising the set of nucleic acid sequences amplified by PCR.) If the complexity is too high, or if the target sequence concentration is too low, the kinetics of hybridization prevent effective enrichment, and the method fails.

Amplicon complexity is reduced in the RDA procedure by the amplification of only a representative subset of all possible fragments from driver and tester. Such subsets are achieved by selective amplification of nucleic acid fragments based on size. Alternatively, the starting nucleic acid can be enriched for target sequences prior to subtraction by partial purification, accomplished by passing the sample through a two-micron filter prior to extraction, thereby eliminating most of the cellular nucleic acids present in the sample and alleviating the necessity of reducing amplicon complexity (Simons et al., *Proc. Natl. Aca. Sci. USA* 92:3401–3405 (1995)).

Other factors also are likely to affect performance in this method. For example, differences in reassociation rates and PCR efficiencies between fragments impose a strong selection for those products most readily formed, regardless of whether or not the sequence is unique to tester. If such a sequence is not unique, it could overwhelm the subtractive capacity of the driver especially in later rounds, resulting in the isolation of sequences that are not specific to, or elevated in, tester-versus-driver. Regardless of their source, such "favored" sequences tend to dominate the enriched fragment population and out-compete tester-unique products that are less efficiently formed, making tester-unique product detection difficult. This problem recently has been approached by isolating the major enrichment products obtained after a series of subtractions and adding them back individually to the driver, thereby boosting the subtractive capacity for those sequences (Ushijima et al., *Proc. Natl. Acad. Sci. USA* 94: 2284–2289 (1997) and Hubank et al., *Nucleic Acids Res.* 22:5640–5648 (1994)). However, a second series of subtractions then must be performed to isolate tester-unique sequences not previously obtained, such as lower copy number sequences or those that amplify relatively poorly.

Problems associated with high amplicon complexity and low copy numbers in the tester have not been fully addressed or resolved. These factors can negatively affect the isolation of sequences by reducing the sensitivity of the subtraction procedure.

In view of the above discussion, it certainly would be advantageous to provide modifications to the subtractive hybridization procedure, including RDA, which would address the problems associated with high amplicon complexity and low copy numbers in the tester.

All U.S. patents and publications are hereby incorporated in their entirety by reference.

SUMMARY OF THE INVENTION

The present invention provides a modified subtractive hybridization method termed Selectively Primed Adaptive Driver-RDA ("SPAD-RDA"), which utilizes a driver-versus-driver subtraction control performed in parallel with the driver-versus-tester subtraction step. The products of the driver control subtraction from each round can be used as the driver of the subsequent round.

This method for performing subtractive hybridization uses a tester sample and a driver sample to determine the presence of a nucleic acid sequence difference in the tester sample. In detail, the method comprises the steps of: (a) separately isolating total nucleic acid from the tester sample and the driver sample, and generating double-stranded cDNA/DNA from the total nucleic acid from the tester sample and the driver sample; (b) digesting the double-stranded cDNA/DNA generated from the tester sample and the driver sample of step (a) with a restriction endonuclease in order to produce a set of restriction fragments for each sample; (c) ligating the driver and tester restriction fragments of each set of step (b) to an oligonucleotide adapter set 1, and amplifying the resulting products with selective primers such that a subset of the restriction fragments of step (b) is amplified;(d) removing the selective primers sequences by restriction endonuclease digestion in order to produce tester and driver amplicons, ligating the 5'-ends of said driver and tester amplicons to an oligonucleotide adapter set 2 to form driver-control and tester, mixing driver-control and tester separately with an excess of non-ligated driver amplicon each, denaturing the resulting mixtures, and allowing the denatured nucleic acid strands within each mixture to hybridize; (e) filling in the 3'-ends of the reannealed driver/tester and the reannealed driver/driver-control using a thermostable DNA polymerase and amplifying resulting sequences; (f) removing remaining single-stranded DNA by digesting with a single-stranded DNA nuclease and amplifying; (g) amplifying double-stranded DNA remaining after nuclease digestion; and (h) cleaving subtraction products of the driver/tester and driver/driver-control with a restriction endonuclease to remove oligonucleotide adapters, and repeating steps (c) through (h), wherein steps (c) through (h) utilize an oligonucleotide adapter set not used in any previous round of RDA, wherein one round consists of performance of RDA steps (c) through (h), and utilize as driver, for each new round of RDA, the restriction endonuclease-cleaved product of the driver/driver-control subtraction from immediately preceeding steps (c) through (h). (Steps (c) through (h) can be repeated for any desired number of times.) In this method, the restriction endonuclease of step (b) and/or step (h) may be a 4–6 basepair recognition site (with an overhanging 5' end, preferably a 4 basepair recognition site. The restriction endonuclease may be, for example, Sau3AI. Although less preferred, any restriction enzyme with a palindromic tetra- or hexanucleotide recognition sequence may be used. The choice of enzyme will affect both amplicon complexity and the design of the oligonucleotide adaptors. Amplicon complexity is increased when a restriction endonuclease with a 4 bp recognition site is used, relative to the complexity obtained when a restriction endonuclease with a 6 bp recognition site is used. This is due to the greater number of amplifiable sequences in the former vs. the latter. Furthermore, the choice of restriction endonuclease affects oligonucleotide adaptor design since the adaptor must be compatible with the sequence and structure present on the ends of the restriction endonuclease digested DNA in order for efficient ligation to occur.

The present invention also includes a method for visual identification of unique tester sequences comprising the steps of: (a) separately isolating total nucleic acid from a tester sample and a driver sample, and generating double-stranded cDNA/DNA from the total nucleic acid from the tester sample and the driver sample; (b) digesting the double-stranded cDNA/DNA generated from the tester sample and the driver sample of step (a) with a restriction endonuclease in order to produce a set of restriction fragments for each sample; (c) ligating the driver and tester restriction fragments of step (b) to an oligonucleotide adapter set 1, and amplifying the resulting products with selective primers such that a subset of the restriction fragments of step (b) is amplified; (d) removing the selective primers sequences by restriction endonuclease digestion in order to produce tester and driver amplicons, ligating the 5'-ends of the driver and tester amplicons to an oligonucleotide adapter set 2 to form driver-control and tester, mixing driver-control and tester separately with an excess of non-ligated driver amplicon each, denaturing said resulting mixtures, and allowing the denatured nucleic acid strands within each mixture to hybridize; (e) filling in the 3'-ends of the reannealed driver/tester and the reannealed driver/driver-control using a thermostable DNA polymerase and amplifying resulting sequences; (f) removing remaining single-stranded DNA by digesting with a single-stranded DNA nuclease and amplifying; (g) placing the driver-tester and driver-control products on a solid substrate; and (h) visually identifying driver tester bands not present in the driver-control bands.

BRIEF DESCRIPTION OF THE DRAWINGS

FIG. 1 presents a diagram exemplifying the PCR priming of a Sau3AI DNA fragment (SEQ ID NO:19 & 21), ligated to the R-BAM adapter set, by (i) oligonucleotide primer R-Bam 24 (SEQ ID NO:1), or by (ii) selective oligonucleotide primer R-BAM19N (SEQ ID NO:20). Boxed sequences are the 4 bp Sau3AI recognition sites, (n) indicates any of the 4 nucleotides and (N) represents the selective base, the complement of (n).

DETAILED DESCRIPTION OF THE INVENTION

Figure 2:
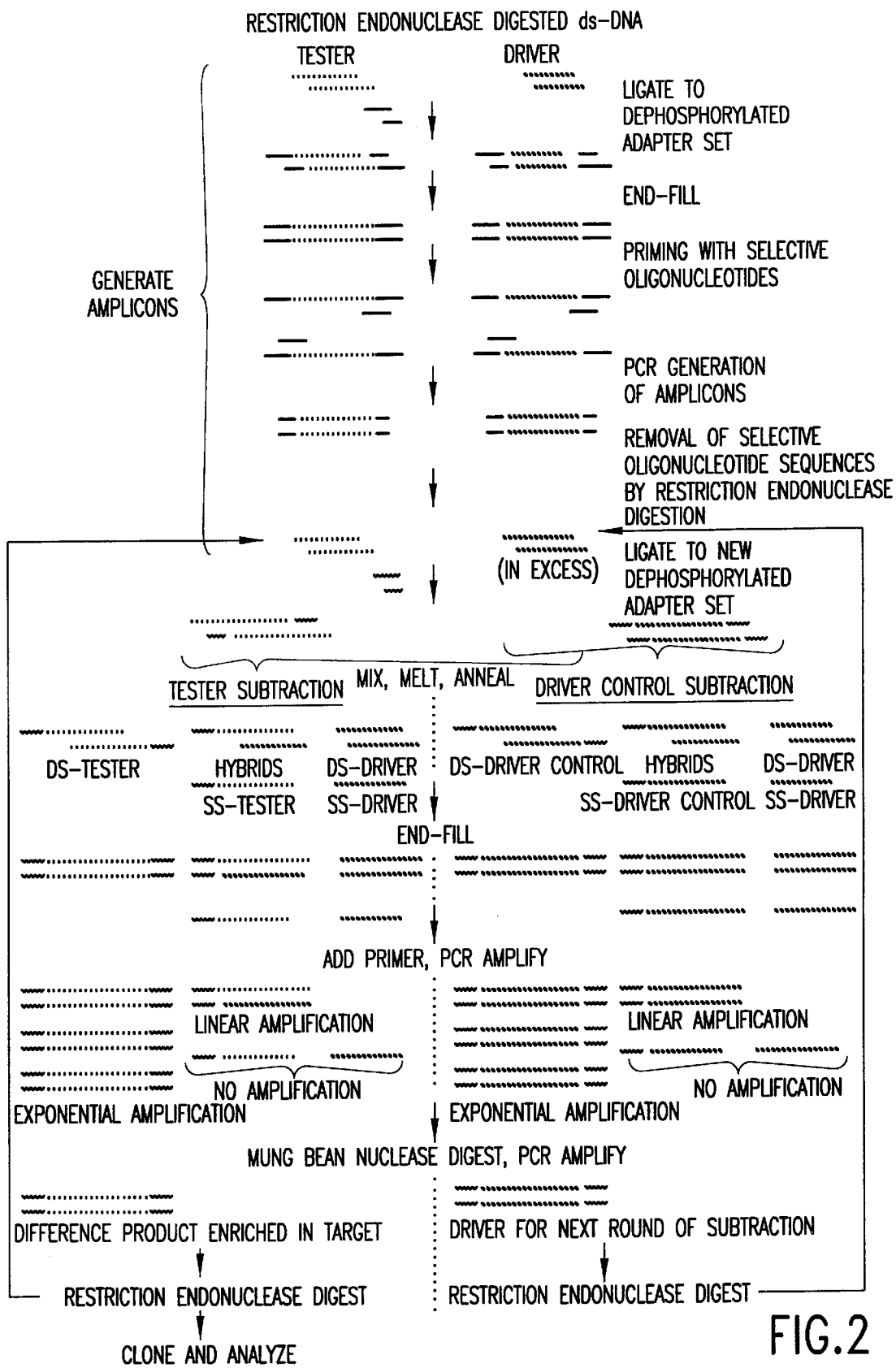
FIG. 2 presents a diagram of the SPAD-RDA procedure of the present invention.

The present invention provides novel modifications to subtractive hybridization methods and, in particular, to the RDA method, resulting in an improved RDA method herein termed "Selectively Primed Adaptive Driver-RDA" ("SPAD-RDA"). The present improved method integrates several modifications into a single protocol. It also demonstrates the improved utility of SPAD-RDA versus unmodified RDA and the effective use of non-paired driver and tester samples in conjunction with SPAD-RDA.

In particular, the present invention demonstrates the use of selective priming to control amplicon complexity for subtractive hybridization methods and, in particular, for RDA, while maximizing the probability that a target sequence will be represented in the tester amplicon. (Examples of oligonucleotide primers containing selective bases at their 3' ends are provided herein. Such primers demonstrate that amplicon complexity can be regulated through primer design.) A different oligonucleotide adapter set for each round of RDA subtraction also is provided by the present invention, along with specific examples of such adapter sets and their use. In addition, the utility of gel filtration chromatography in the RDA method is shown, both for removal of competing primers prior to selective priming of amplicons and for removal of cleaved adapter sequences to prevent their interference with ligation of a new adapter set. Further, an adaptive driver strategy for subtractive hybridization methods, in particular for RDA, is provided, in which the products of a driver versus driver control subtraction are used as driver for the subsequent round. The use of the driver control as a visual reference to aid in identification of tester-unique fragments also is provided.

Furthermore, in the present invention, the role of product analysis is expanded by applying immunoscreening and differential hybridization strategies to the detection of tester-unique sequences in the subtraction products.

The method of the present invention has several uses. It can be utilized to determine whether an infectious agent is present in a test sample by using a pre-inoculation (or a pre-infection) sample as the driver and a post-inoculation (or post-infection) sample as the tester. In addition, the method described herein can be used for genetic testing to identify a marker associated with an individual's predisposition to a disease or to determine the alteration of a gene wherein detection of the alteration itself is diagnostic of the disease. In these determinations, a pooled normal sample serves as the driver, and the patient sample is used as the tester.

Various test samples that can be utilized by the present invention include but are not limited to body fluids such as whole blood, serum, plasma, and urine. Other samples, such as tissues, also can be utilized, or any sample from which nucleic acids can be extracted. It also is within the scope of the present invention that cell cultures and/or cell supernatants may be utilized.

Prior to presenting the examples illustrating the present invention, details have been set forth as follows concerning the materials and methods utilized in the examples:

Materials and Methods

General Techniques. Conventional and well-known techniques and methods in the fields of molecular biology, microbiology, and recombinant DNA technology are employed in the practice of the present invention unless otherwise noted. These techniques and methods are explained and detailed in the literature and standard textbooks and are therefore known to those of ordinary skill in the art. (See, for example, J. Sambrook et al., "Molecular Cloning: A Laboratory Manual," $2^{nd}$ edition, Cold Spring Harbor Press, Cold Spring Harbor, N.Y. (1989)). The conventional RDA procedure is limited to identifying and cloning differences only in double-stranded DNA between complex, yet similar, DNA backgrounds of Lisitsyn et al., Science 259:946–951 (1993). These differences can include any large DNA virus (e.g., >25,000 base pairs ["bp"] DNA) that is present in a test sample such as a cell line, blood, plasma or tissue sample. A modification of RDA described by Simons et al., supra and Hubank et al., supra broadened the conventional RDA procedure to include RNA and/or single-stranded DNA by converting them to double-stranded DNA and incorporating them into the driver and tester. This previous modification also increased the complexity of the nucleic acid sequences being subjected to RDA by fragmenting the DNA with a restriction enzyme that had a 4 bp recognition site, as opposed to restriction enzymes that had a 6 bp recognition site, as was used in conventional RDA. These modifications increased the probability of detection/isolation of smaller viral genomes (e.g., 15,000 bases), especially those of RNA or single-stranded DNA.

At least one previous report (Lisitsyn et al., supra (1993)) demonstrated that increased complexity could result in reduced sensitivity for the detection of tester-specific sequences, indicating that a sequence that was present in low copy number, such as a low titer virus, would be difficult to detect. The present invention overcomes the problems of the conventional RDA procedure and the modifications by Simons et al. and Hubank et al. by allowing the detection of viruses at lower titers or viruses with a small genome, in a straightforward manner.

The method of the present invention is set forth in FIG. 2. In one example provided herein, viral sequences were isolated from a sample known to contain hepatitis C virus (i.e., an RNA virus). The isolation and cloning of HCV sequences were achieved by modifying the conventional RDA procedure as described by Lisitsyn et al., supra (1993).

Referring to FIG. 2, the two genomes under evaluation were designated as the "tester" (the post-infection serum known to contain HCV) and the "driver" (a pre-infection serum from the same individual without HCV). First, total nucleic acid (DNA and RNA) was isolated from the tester sample and the driver sample (not shown), by using a commercially available kit for total nucleic acid isolation (available from United States Biochemical [USB], Cleveland, Ohio). Alternatively, a DNA-only or an RNA-only extraction procedure can be utilized, as known and described in the art.

In the conventional RDA procedure, the sample of driver and tester are obtained from the same source since the basis of the method is a comparison and subtraction of common nucleic acids. However, in contrast, in accordance with the present invention, it may be possible to use highly related, but non-identical, material for the source of the tester and driver nucleic acids. By "highly related, but non-identical" is meant >95% sequence identity using standardized programs known in the art.

Double-stranded DNA was generated from the total nucleic acid by random primed reverse transcription of the RNA, followed by random primed DNA synthesis. This treatment converted RNA and single-stranded DNA to double-stranded DNA molecules amenable to RDA.

Next, the double-stranded tester and driver DNAs were amplified to generate an abundant amount of starting material. This was achieved by cleaving double-stranded DNA prepared as described hereinabove with a restriction endonuclease that had a 4 bp recognition site (in this example, with Sau3AI). The DNA fragments (FIG. 2, top) were ligated to oligonucleotide adapters (termed "set #1"), end-filled and PCR amplified using selective primers. The design of the selective primers (i.e., R-Bam 19C and R-Bam 19G) was such that only a subset of all the restriction fragments present would be amplified, thereby reducing the amplicon complexity. FIG. 1 presents a diagram exemplifying the PCR priming of a SAU3AI DNA fragment, ligated to the R-Bam adapter set, by (i) oligonucleotide primer R-Bam 24, or by (ii) selective oligonucleotide primer R-Bam19N. Boxed sequences appearing in FIG. 1 are the 4 bp Sau3AI recognition sites, (n) indicates any of the 4 nucleotides and (N) represents the selective base, the complement of (n). Referring back to FIG. 2, following PCR amplification, the selective primer sequence was removed by restriction endonuclease digestion (in this example, with Sau3AI), which liberated a large amount of tester and driver nucleic acid (i.e., amplicons), which could then be used in the first round of subtractive hybridization.

The remaining steps depicted in FIG. 2 were designed to enrich for DNA sequences unique to the tester. This was accomplished by combining subtractive hybridization and kinetic enrichment into a single step. Briefly, an oligonucleotide adapter set (termed "set #2") was ligated to the 5'-ends of a portion of the driver (henceforth designated "driver-control") and tester amplicons. Driver-control and tester ligated to adapter set #2 were then mixed separately with an excess of non-ligated driver amplicon, denatured, and allowed to hybridize under standard conditions for at least 20 hours. It was hypothesized that a large amount of the sequences that were held in common between the tester and the driver amplicons would anneal during this time; the same was thought to be true of the driver/driver-control hybridization mix. It was also thought that sequences that were unique to the tester amplicon would reanneal.

The 3'-ends of the reannealed driver/tester DNA hybridization and the reannealed driver/driver-control DNA hybridization were filled in using a thermostable DNA polymerase at elevated temperature, as is known and described in the art. The reannealed sequences that were unique to the tester contained the ligated adapter on both strands of the annealed sequence. Thus, 3' end-filling of these molecules created sequences complementary to PCR primers on both DNA strands. As such, these DNA species were amplified exponentially when subjected to PCR. A low level of tester:tester or driver-control:driver-control hybrids formed for sequences that were held in common with the driver. These DNA species also were amplified exponentially. In contrast, a relatively large amount of hybrid molecules, in which one strand was derived from the tester or driver-control and one strand was derived from the driver amplicon, amplified linearly when subjected to PCR. This occurred because only one strand (derived from the tester or driver-control) contained the ligated adapter sequence, and 3'-end filling only generated sequences complementary to the PCR primer on the strand derived from the driver amplicon.

Next, the double-stranded DNA of interest (i.e. primarily tester-unique sequence) was enriched quantitatively using PCR for 10 cycles of amplification. Remaining single-stranded DNA was removed by single strand DNA nuclease digestion, using mung bean nuclease, as previously described in the art. Double-stranded DNA, remaining after nuclease digestion, was PCR amplified an additional 17 to 27 cycles.

Finally, the subtraction products of the driver/tester and driver/driver-control hybridizations were cleaved with restriction endonuclease (e.g., Sau3A I) to remove the oligonucleotide adapters (FIG. 2, bottom). A portion of these DNA products was then subjected to additional rounds of subtraction and amplification (beginning with the ligation of an oligonucleotide adapter set not used in any previous round of RDA). The driver for each new round of RDA was the restriction endonuclease cleaved product of the driver/driver-control subtraction from the previous round (e.g., first round driver/driver-control products are recycled as driver in the second round, etc.).

These described modifications to known RDA procedures relate to the preparation of amplicons of reduced complexity for both tester and driver DNA, additional RDA adapter sets, spin column purification of restriction endonuclease digests, and use of a recyclable driver. Since RDA sensitivity has been reported to be inversely proportional to amplicon complexity, how that complexity is controlled is an important aspect of the procedure. RDA amplicons previously were derived from DNA that had been digested with a restriction endonuclease having a 4-base or a 6-base recognition site. Thus, only those fragments that were short enough to be efficiently amplified by PCR were well-represented in the amplicon, thereby reducing amplicon complexity. Theoretically, when the amplicon complexity remains relatively high (as is the case with a 4-base recognition enzyme), the sensitivity of the RDA would be diminished. Conversely, if a 6-base recognition enzyme were used, fewer fragments would be generated and their average length would be greater. This results in an amplicon of lower complexity but also increases the probability that target fragments would be insufficiently amplified to be functionally represented in the tester amplicon. Thus, longer tester-unique sequences may be at too low a copy number relative to other sequences present in the amplicon, due to the tendency of PCR to favor amplification of shorter sequences, thereby leading to loss of such longer sequences from the amplicon. Thus, previously described RDA methods may not have detected target sequence if the target sequence was present at low copy number (e.g., a low titer virus) or if the restriction sites were spaced too far apart.

In view of the above, it was thought that the use of one or more selective PCR primers would allow more precise regulation of amplicon complexity in the method of the present invention. This regulation could therefore permit one to generate amplicons using restriction enzymes that cleaved more frequently (i.e. 4-base recognition sites), while maintaining a reduced amplicon complexity more similar to restriction enzymes that cleaved less frequently (i.e., 6-base recognition sites). Therefore, selective priming would be achieved through the use of a specific 3'-base(s) (designated "selective base") on the PCR primer that was used to generate the amplicons. In theory, only those restriction fragments that have bases complementary to the selective base at the 3'-end of both strands would be amplified (TABLE 1 and FIG. 1).

TABLE 1

Effect of Selective Priming on Amplicon Complexity

| | Total Number of Fragments[b] | | Number of Sau3AI Fragments Amplified with Selective Priming[c] | |
|---|---|---|---|---|
| Genome Size[a] | BamHI | Sau3AI | Single (6.25%) | Double (25%) |
| 4.1 × 10$^9$ bp | 1 × 10$^6$ (Avg. 4096 bp) | 1.6 × 10$^7$ (Avg. 256 bp) | 1 × 10$^6$ | 4 × 10$^6$ |
| 12300 bp | 3 (Avg. 4096 bp) | 48 (avg. 256 bp) | 3 | 12 |

[a]Theoretical example of a small viral genome (12300 bp) in the presence of a large genome (4.1 × 109 hp) background
[b]Total number of restriction fragments generated by cleavage with BamHI (6 bp recognition site) or Sau3AI (4 bp recognition site), and the average fragment size for each (assuming a random base distribution).
[c]Calculated number of all Sau3AI fragments (% of total) that would be amplified by a primer containing a single unique 3' selective base, or by a primer containing a double selective base (i.e. either of two bases are equally present at the 3'-end).

In view of the results presented in Table 1, amplicon complexity should be reduced through specific amplification of a subset of all possible restriction fragments, not by size selection based on PCR efficiency.

In the past, only three oligonucleotide adapter sets were used for RDA. One set was for the generation of the amplicons, and the other two sets were alternated between consecutive rounds of RDA. Therefore, whenever more than two rounds of subtraction were performed, an adapter set from a previous round would have to be reused. It was observed that RDA subtraction products can have an oligonucleotide adapter set from a previous round attached to them. This can become a problem since such carryover products would be amplified whenever the homologous adapter set was reused, thus bypassing the requirement for proper hybrid formation and in so doing reducing subtraction efficiency. For this reason, a new oligonucleotide set was used for each new round of RDA. Thus, even though adapter set carryover may occur, these fragments will only be amplified if they participate in the subtractive hybridization step.

In partial response to the adapter set carryover problem described above, all restriction enzyme digests were purified by passaging these digests through a gel filtration spin column prior to ligation of a new adapter set. It was believed that this would greatly reduce the concentration of free adapters cleaved off by the restriction enzyme, thus preventing them from participating in the subsequent ligation reaction. Furthermore, during the initial generation of driver and tester amplicons, spin column purification was used to reduce the level of non-ligated oligonucleotide set #1 so that it would not compete with the selective PCR primers. Finally, it was thought that spin column purification would help to eliminate very small PCR products, such as primer dimers, which can out-compete the larger desired products. In this respect, such spin column purification is similar in purpose to the size selection step performed by gel electrophoresis on the tester amplicon as previously described in the art, except that selection against small PCR products is maintained throughout the procedure, not just at the beginning. Thus, the ability to select against small PCR products is an improvement heretofore not realized by known RDA methods.

As RDA is currently practiced, the driver amplicon is generated once at the beginning of the procedure and used for subtraction against both the tester amplicon and the difference product from all subsequent rounds. However, after the first round of RDA, the driver no longer accurately reflects the relative composition of the subtraction product with respect to common sequences. The result using current RDA methodology is that with each round of subtraction, the driver becomes less and less effective. Therefore, a shortcoming of the presently known RDA methods is that sequences common to driver and tester that are inefficiently subtracted can be incorrectly isolated as tester-unique sequences by RDA.

It was decided that a driver was needed that could more accurately represent the composition of the subtraction product after each round. To accomplish this, a control subtraction (driver vs. driver) was developed which was performed in parallel with the driver vs. tester subtraction (see FIG. 2). The product of this control subtraction was used as driver for the subsequent round. This ability to utilize a control subtraction provides a source of variable driver throughout the procedure that accurately represents those fragments held in common with the driver/tester subtraction product. An additional advantage is that by comparison to the driver/tester subtraction product, the driver control provides a visual reference to assist in the identification of those fragments that are tester-specific. This is analogous to the side-by-side comparison of two samples performed in nucleic acid fingerprinting procedures to identify sequences unique to one of the samples, an option not previously available to RDA methods since it was heretofore unknown how such a reference could be generated for RDA.

The present invention will now be described by way of examples, which are meant to illustrate, but not to limit, the spirit and scope of the invention.

EXAMPLES

The examples provided below describe in detail the application of the SPAD-RDA method of the invention and subsequent product screening procedures to the isolation of viral sequences from plasma. Initially, a demonstration of SPAD-RDA was performed on plasma samples containing a known virus and the subtraction products were then screened for the presence of the virus by a variety of techniques. The effectiveness of the combined methods is compared to that of the unmodified conventional RDA method of Lisitsyn for the isolation of viral sequences when applied to the same samples. Furthermore, utility of the SPAD-RDA method in isolating sequences of a heretofore unknown viral genome is demonstrated.

Example 1

HCV Samples

A. Animal Inoculation (Colonel). An acute phase liver homogenate from a passage 2 chimpanzee infected with HCV (Hutchinson strain) was inoculated intravenously into chimpanzee CH117. This resulted in a chronic infection in CH117. CH117 serum (10 ml), obtained 945 days post-infection from this animal, then was inoculated intravenously into chimpanzee CH427. This resulted in an acute infection in CH427 that resolved within three months. Plasma samples were collected from CH427 before initial inoculation, and then at intervals of every few days while ALT levels were significantly elevated (see G. G. Schlauder et al., *J. Clin. Microbiol.* 29:2175–2179 (1991)).

B. HCV Sequence. The complete HCV genome of virus-derived cDNA from CH427 was sequenced and has been deposited in GenBank under the HCV Colonel Accession Number AF290978.

Example 2

Subtractive Hybridization of Paired Samples Using Reduced Complexity Amplicons and a Recycled Driver Control A. Generation of Double-Stranded DNA for Amplicons. Using the amplicon procedure described hereinabove in Materials and Methods, tester amplicon was prepared from total nucleic acid obtained from a pool of acute-phase CH427 plasma samples that were obtained 49, 54, 56, 61, 66, 68, 77, and 84 days post inoculation and which previously were shown by RT-PCR to contain HCV RNA (G. G. Schlauder et al., supra). Driver amplicon then was prepared from total nucleic acid obtained from a pre-inoculation CH427 plasma sample, as follows. Briefly, 100 $\mu$l of each plasma was extracted using a commercially available kit (e.g., a kit available from United States Biochemical [USB], Cleveland, Ohio, catalog number 73750), and 10 $\mu$g yeast tRNA were added as a carrier. This nucleic acid mixture was subjected to random primed reverse transcription followed by random primed DNA synthesis. Briefly, an 80 $\mu$l reverse transcription reaction was performed utilizing an RNA PCR kit (available from Perkin Elmer, Norwalk, Conn., catalog number N808-0017) as directed by the manufacturer, using random hexamers and incubating reactions for 10 minutes at 20° C. followed by 1 hour incubation at 42° C. The reactions were then terminated and cDNA/RNA duplexes denatured by incubation at 99° C. for 2 minutes. The reactions were supplemented with 10 $\mu$l 10×RP buffer (containing 100 mM NaCl, 420 mM Tris [pH 8.0], 50 mM DTT, 100 mg/ml BSA), 250 pmoles random hexamers and 13 units Sequenase® version 2.0 polymerase (available from USB, catalog number 70775) in a total volume of 100 $\mu$l. The reactions were incubated at 20° C. for 10 minutes, followed by incubation at 37° C. for 1 hour. After phenol/chloroform extraction and ethanol precipitation, the double stranded DNA products of these reactions were digested with 4 units of restriction endonuclease Sau3AI (available from New England Biolabs [NEB], Beverly, Mass., catalog number 169L) in 30 $\mu$l reaction volumes for 30 minutes, as directed by the supplier.

B. Generation of Amplicons. Sau3AI-digested DNA was extracted and precipitated as described above. The entire Sau3AI-digested product was annealed to 465 pmoles R-Bam 24 (SEQUENCE ID NO: 1) and 465 pmoles R-Bam 12 (SEQUENCE ID NO: 2) in a 30 $\mu$l reaction volume buffered with 1×T4 DNA ligase buffer (available from NEB) by placing the reaction in a 50–55° C. dry heat block, which was then incubated at 4° C. for 1 hour. Annealed product was ligated by adding 400 units T4 DNA ligase (available from NEB, catalog number 202S). After incubation for 14 hours at 16° C., 20 µl water was added to the ligation reaction, and the entire 50 µl reaction was purified over a PCR SELECT® spin column (available from 5 Prime, 3 Prime, Boulder, Colo., catalog number 1-829527) as described by the supplier. A small scale PCR was performed on the eluate from the spin column, as follows. Briefly, 20 µl of the spin column eluate was added to 42 µl H$_2$O, 18 µl 5×PCR buffer (335 mM Tris, pH 8.8, 80 MG [NH$_4$]$_2$SO$_4$, 20 mM MgCl$_2$, 0.5 mg/ml bovine serum albumin, and 50 mM 2-mercaptoethanol), 8 µl dNTP stock (4 mM each), 1 µl (62 pmoles) R-Bam 19C (SEQUENCE ID NO: 3) and 1 µl (62 pmoles) R-Bam 19G (SEQUENCE ID NO: 4).

PCR amplification was performed in a GeneAmpR 9600 thermocycler (available from Perkin Elmer, Foster City, Calif.). Samples were incubated for 3 minuses at 72° C., after which time 10 µl of an Amplitaq dilution (3.75 units Amplitaq® [available from Perkin Elmer, catalog number N808-1012] in 1×PCR buffer) (see above) was added. Incubation was continued for 5 minutes at 72° C. to fill in the recessed 3'-ends of the ligated adaptors. The samples were amplified for 30 cycles (30 seconds at 95° C., 30 seconds at 60° C., 1 minute at 72° C.) followed by a final 10 minute extension at 72° C.

After agarose gel confirmation of successful amplicon generation (i.e., products ranging from approximately 100 bp to over 1500 bp), a large scale amplification of tester and driver amplicons was performed. Twelve 100 µl polymerase chain reactions (PCRs) and eight 100 µl PCRs were set up as described above for the preparation of small scale driver and tester amplicons, respectively, except that the Amplitaq polymerase was added at room temperature. Two µl from the small scale PCR product per 100 µl reaction volume served as the template for the large scale amplicon generation. Thermocycling was performed as described above for an additional 20 cycles of amplification, except the end-filling step at 72° C. was omitted. The PCR reaction for both driver and tester DNA were then phenol/chloroform extracted twice, isopropanol precipitated, washed with 70% ethanol, digested with Sau3AI to remove the selective primer sequences, extracted again, precipitated and washed. Ten µg of each was spin column purified as above. Driver purified through the spin column is designated as Driver Control (DC) whereas the Sau3AI digested driver, prior to column purification, is designated as D.

C. Hybridization and Selective Amplification of Amplicons. One µg of spin column eluate from tester (T) and DC were separately ligated to J-Bam 24 (SEQUENCE ID NO: 5) and J-Bam 12 (SEQUENCE ID NO: 6) as described above. After completion of the reaction, ligase activity was eliminated by incubation of the samples at 67° C. for 10 minutes. For the first subtractive hybridization, D amplicon (40 µg) was added to both the DC (0.5 µg) and T (0.5 µg) amplicons ligated to the J-Bam adapter set, to form mixtures DC-1 and D/T-1, respectively (80/1 ratio). DC-1 and D/T-1 were phenol/chloroform extracted, ethanol precipitated and washed as above, and the DNA was resusupended in 4 µl of EE×3 buffer (30 mM EPPS, pH 8.0 at 20° C. [available from Sigma, St. Louis, Mo.], 3 mM EDTA), then overlaid with 40 µl of mineral oil. Following heat denaturation (3 minutes at 99° C.), 1 µ(l) of 5 M NaCl was added, and the DNA was allowed to hybridize at 67° C. for 22 hours.

The aqueous phase was removed to a new tube and 95 µl of TE buffer (10 mM Tris, pH 7.4 and 1 mM EDTA) was added to the sample and mixed. Eleven µl of the diluted hybridization mix were added to 293.7 µl H$_2$O, 88 µl 5×CR buffer (above), 35.2 µl dNTP stock (4 mM each) and 3.3 µl (16.5 units) Amplitaq® polymerase. This solution was divided into two aliquots (196 µl each) and incubated at 72° C. for 5 minutes to fill in the 5' overhangs created by the ligated J-Bam 24 primer. Four µl of J-Bam 24 (SEQUENCE ID NO: 5, 248 pmoles) were added per tube and each 200 µl reaction was split into two aliquots (100 µl each) at 72° C. The samples were amplified for 10 cycles (30 seconds at 95° C., 1 minute at 70° C.) followed by a final extension at 72° C. for 10 minutes. DC-1 and D/T-1 were pooled separately, phenol/chloroform extracted twice, isopropanol precipitated, washed with 70° C. ethanol, and then resuspended in 34 µl H$_2$O.

Single-stranded DNA was removed by mung bean nuclease (MBN), as follows. Briefly, the amplified DNA was digested with 20 units MBN (available from NEB, catalog number 250S) in a 40 µl reaction as described by the supplier. One hundred and sixty µl 50 mM Tris, pH 8.9 was added to the MBN digest and the enzyme inactivated at 99° C. for 5 minutes. Forty one µl of MBN-digested DNA were added to 242.9 µl H$_2$O, 82 µl 5×PCR buffer (above), 32.8 µl dNTP stock (4 mM each) and 3.1 µl (15.5 units) Amplitaq® polymerase and 8.2 µl J-Bam 24 (SEQUENCE ID NO: 5, 508 pmoles). This solution was divided into 4 aliquots (100 µl each) and amplified for 17 cycles (30 seconds at 95° C., 1 minute at 70° C.) followed by a final extension at 72° C. for 10 minutes. Amplified DC-1 and D/T-1 were pooled, and the products visualized by agarose gel electrophoresis. The pooled samples were phenol/chloroform extracted twice, isopropanol precipitated, washed as above, then resuspended in H$_2$O. The amplified DNA (40 µg) was digested with Sau3AI, extracted and precipitated as described above. The pellets were each resuspended in 26 µl H2O. Ten µg of each were spin column purified as above.

Next, a large scale DC-1 preparation was prepared for use as driver in the second round of subtraction. In particular, the DC-1 mung bean nuclease digest (162 µl) was added to 960 µl H$_2$O, 324 µl 5×PCR buffer (above), 129.6 µl dNTP stock (4 mM each) and 12.25 µl (15.5 units) AmplitaqR polymerase and 32.4 µl J-Bam 24 (SEQUENCE ID NO: 5, 2000 pmoles). This solution was divided into 16 aliquots (100 µl each) and amplified for 17 cycles as described above. The reactions were pooled, phenol/chloroform extracted twice, isopropanol precipitated, washed, resuspended in H$_2$O, digested with Sau3AI, extracted again and precipitated as described above. The final pellet was resuspended in 256 µl H$_2$O.

D. Subsequent Hybridization/Amplification Steps. One µg of the spin column purified DNA (DC-1 and D/T-1) from the previous hybridization/selective amplification was ligated to the N-Bam adapter set (SEQUENCE ID NO: 7 and SEQUENCE ID NO: 8) as described previously. For the second subtractive hybridization, DC-1 driver (40 µg) was added to both the DC-1 (50 ng) and D/T-1 (50 ng) products previously ligated to the N-Bam adapter set, to form mixtures DC-2 and D/T-2, respectively (800/1 ratio). The hybridization and amplification procedures were repeated as described above except that hybridization was for 90 hours at 67° C., the PCR primer sed was N-Bam 24 (SEQUENCE ID NO: 7), the extension temperature during the thermocycling was 72° C. and the final amplification (after MBN digestion) was for 20 cycles. A large scale DC-2 preparation analogous to the DC-1 driver above was generated for use as third round driver.

One µg of the spin column purified DNA (DC-2 and D/T-2) from the previous hybridization/selective amplification was ligated to the F-Bam adapter set (SEQUENCE ID NO: 9 and SEQUENCE ID NO: 10) as described previously.

For the third subtractive hybridization, DC-2 driver (40 μg) was added to both the DC-2 (4 ng) and D/T-2 (4 ng) products ligated to the F-Bam adapter set, to form mixtures DC-3 and D/T-3, respectively ($10^4/1$ ratio). The hybridization and amplification procedures were repeated as described above except that hybridization was for 21 hours at 67° C., the PCR primer used was F-Bam 24 (SEQUENCE ID NO: 9), extension temperature during thermocycling was 72° C., and the final amplification (after MBN digestion) was for 23 cycles. A large scale DC-3 preparation analogous to the DC-1 driver described above was generated for use as fourth round driver.

One μg of the spin column purified DNA (DC-3 and D/T-3) from the previous hybridization/selective amplification was ligated to the S-Bam adapter set (SEQUENCE ID NO: 11 and SEQUENCE ID NO: 12) as described previously. For the fourth subtractive hybridization, DC-3 driver (40 μg) was added to both the DC-3 (400 pg) and D/T-3 (400 pg) products ligated to the S-Bam adapter set, to form mixtures DC-4 and D/T-4, respectively ($10^5/1$ ratio). The hybridization and amplification procedures were repeated as described above, except that hybridization was for 94 hours at 67° C., the PCR primer used was S-Bam 24 (SEQUENCE ID NO: 11), extension temperature during the thermocycling was 72° C. and the final amplification step after MBN digestion was for 27 cycles.

E. Cloning of the Difference Products. Three bands from the fourth round of subtraction, which appeared to be present in D/T-4 but not in DC-4, were excised from a 2% agarose gel as described in Materials and Methods, supra, and purified using the GENECLEAN II Kit (BIO 101, San Diego, Calif., cat #1001-400) as directed by the supplier. These difference products, previously digested with Sau3AI, were cloned into the BamHI site of pUC18 using the Ready-To-Go ligation kit (Pharmacia, Piscataway, N.J., cat. #27-5260-01), as directed by the supplier. One half μl of the ligation reactions was used to transform *E. coli*-competent XL-1 Blue cells (available from Stratagene, La Jolla, Calif., cat. #200236), as directed by the supplier. The transformation mixtures were plated on LB plates supplemented with ampicillin (150 μg/ml) and incubated overnight at 37° C. Thirty-six of the resulting colonies were grown up in liquid culture, and plasmid miniprep DNA was prepared as directed using the Wizard 373 DNA Purification System (available from Promega, Madison, Wisc., cat. #A7030).

In addition to the cloning of the three Sau3AI fragments from the fourth round products described above, 50 ng of the entire population of products from the fourth round (uncut) were ligated into a PCR product cloning vector using the pT7Blue T-Vector Kit plus Ligase (available from Novagen, Madison, Wisc., cat. #6983-1) as directed by the supplier. One μl of the ligation product was used to transform *E. coli*-competent XL-1 Blue cells as before, and another 36 plasmid minipreps were prepared from the resulting colonies as described above.

Example 3
Identification of HCV Clones and DNA Sequence Analysis

In general, a dot blot of all 72 minipreps from Example 2 was prepared and hybridized versus an HCV genome probe. Briefly, 0.5 μl of each plasmid preparation was spotted onto a Hybond-N filter (available from Amersham, Arlington Heights, Ill., cat.# RPN2020B ), denatured, neutralized, UV cross-linked and dried with heat under a vacuum, as directed by the supplier. The dot blot was pre-hybridized, hybridized with a $^{32}$P-labeled probe covering the entire HCV genome, washed and exposed, as described and known in the art.

A subset of those clones positive for HCV inserts (13 of 43) was analyzed further by DNA sequencing using the ABI automated sequencing method, as well-known in the art (see, e.g., Muerhoff et al., *J. Virol.* 71:6501–6508 (1997)). These sequences fell into five non-overlapping consensus groups, each of which was searched against the GenBank database using the BLASTN algorithm (Altschul et al, *J. Mol. Biol.* 215:403–410 [1990]). The BLASTN search (Wisconsin Sequence Analysis Package, Genetics Computer Group, Madison, Wisc.; default parameters (i.e., wordsize= 11, match=1, mismatch=−3, gapweight=10, lengthweight= 1)) demonstrated a high degree of sequence similarity to hepatitis C virus for all 5 groups. Consensus sequences were homologous to the following five Sau3AI fragments, predicted from the CH427 HCV Genbank sequence: (1) bases 3515 to 3955, (2) 3952 to 4161, (3) 6470 to 6683, (4) 6680 to 6867, and (5) 6864 to 7101. These sequences (1285 nucleotides total) encompassed 13.7% of the CH427 HCV genome.

Of the 25 Sau3AI fragments present in the CH427 HCV sequence, four were completely compatible with the selective primer sequence (i.e., both ends of the fragment can correctly pair with the 3'-base of one or the other selective primer). It was theorized that one of these four probably would not be efficiently amplified due to its size (1800 bp) and so would not be represented in the original amplicon. This left three fragments predicted to be isolated by SPAD-RDA, two of which were obtained (67%). The remaining three Sau3AI fragments isolated by the method of the invention were not predicted and may indicate that selective priming was not 100% specific. For each of these, however, one end was compatible with the selective primers (3 of 12, or 25%), while none of the remaining nine fragments with two non-compatible ends were isolated (0%). Thus, it appears that reduction of amplicon complexity by selective priming of Sau3AI fragments was effective. By contrast, if the amplicons were comprised of BglII, BamHI or HindIII fragments [as described by Lisitsyn et al., supra (1993a)], no HCV fragments would have been isolated. The CH427 sequence is known to contain only one (BamHI, HindIII) or two (BglII) of each of these enzyme recognition sites, and none of the predicted fragments would be amplifiable.

Example 4
Subtractive Hybridization of Paired Samples Using Complex Amplicons and a Single Driver A. Generation of Double-Stranded DNA for Amplicons. Double-stranded DNA for D and T were prepared as described above in Example 2.

B. Generation of Amplicons. D and T amplicons were prepared as described above in Example 2, except for three exceptions. First, R-Bam 24 (SEQUENCE ID NO:1) was used for PCR priming in both the small and large scale amplicons at a concentration of 124 pmoles per 100 μl PCR (not 62 pmoles of each of R Bam 19C and R Bam 19G, concentrations previously used in Example 2). Second, the large scale D amplicon preparation consisted of 16×100 μl PCR reactions (not 12, as previously used in Example 2). Third, only T was ligated to the J Bam adapter set (no DC subtraction was performed in parallel, as was previously performed in Example 2).

C. Hybridization and Selective Amplification of Amplicons. Four rounds of subtractive hybridization were performed as described above in Example 2, except the driver for each round was D (not the DC subtraction product from the previous round).

Example 5
Comparison of RDA Methods

Southern blot hybridizations were performed according to standard procedures as described in the art (see, e.g., Sambrook et al. Molecular Cloning: A Laboratory Manual, 2$^{nd}$ ed. Cold Spring Harbor Laboratory Press, Cold Spring Harbor, N.Y. (1989)) to compare the performance of SPAD-RDA described herein versus that of the RDA method previously described by Lisitsyn et al., *Science* 259:946–951 (1993). Briefly, 400 to 500 ng DNA of Sau3AI digested driver, tester and the products from all four rounds of subtraction were electrophoresed on three separate 2% agarose gels: one gel each for the two different methods and one summary gel for side-by-side comparison. Following transfer, the blots were pre-hybridized, hybridized with a $^{32}$P-labled probe covering the entire HCV genome, washed and exposed.

Figure 3A:
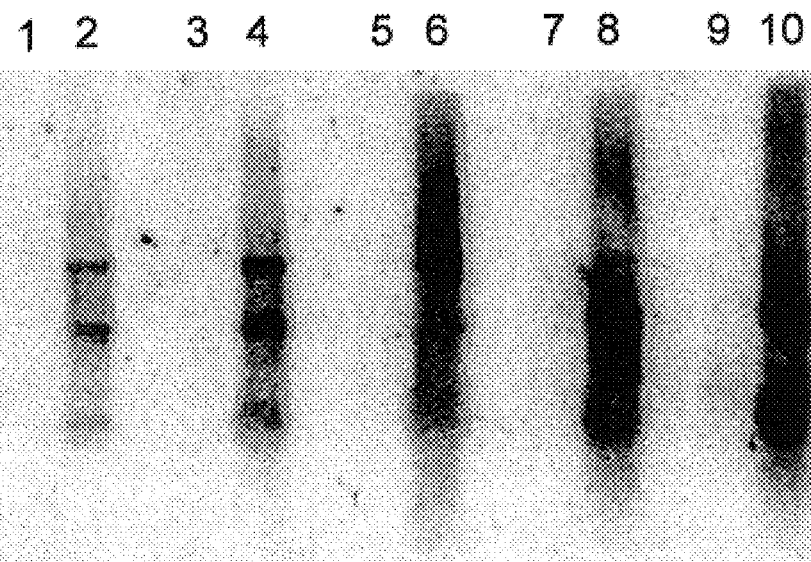
FIG. 3 presents Southern blots that demonstrate the enrichment for HCV sequences by the traditional RDA method of Lisitsyn et al. (*Science* 259:946–951 (1993)) versus the SPAD-RDA method of the present invention.
Figure 3B:
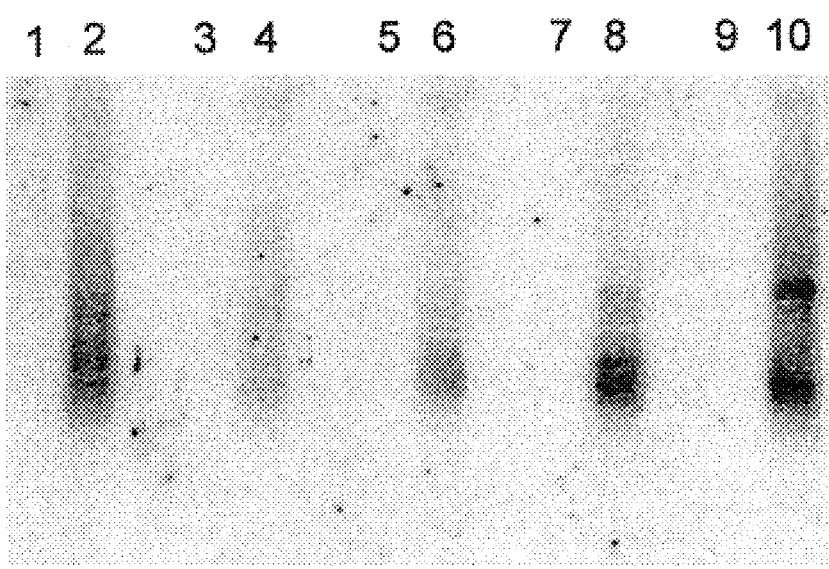

For both methods, an increase was observed in sequences that hybridized to the HCV probe, especially in the later rounds (FIG. 3). However, none of the ethidium bromide (EtBr) stained bands seen in the traditional RDA products appeared to correspond to a HCV hybridizing sequence, suggesting that such sequences were still rare after four rounds of enrichment. In contrast, three EtBr stained bands seen in the SPAD-RDA method hybridized to the HCV probe, which indicated that they were major products of the enrichment process. Furthermore, all three EtBr bands were unique to the tester/driver subtraction as compared to the driver control, which demonstrated that even in the absence of probe hybridization data, HCV sequences would be readily isolated.

Example 6
Subtractive Hybridization of Non-Paired Samples Using Reduced Complexity Amplicons and a Recycled Driver Control One of the major limitations of conventional RDA for the isolation of infectious agents is the requirement that paired nucleic acid samples be available for the preparation of tester and driver amplicons. In cases of infectious agents afflicting humans, these paired samples are rarely available in the absence of an established animal model. Thus, if attempting to utilize samples from two individuals when performing the conventional RDA method, it is virtually impossible to prepare identical amplicons. Therefore, isolated sequences would represent polymorphic differences between the two individuals. In fact, the original description of RDA demonstrated the isolation of polymorphic differences between two related individuals (Lisitsyn et al., supra (1993)).

It was thought that, by significantly reducing the complexity of an amplicon, it would be possible to prepare virtually identical amplicons from two distinct nucleic acid sources. Thus, upon performing a series of subtraction and amplification cycles, the sequences isolated would represent authentic differences between the two sources, and not polymorphic variants, as heretofore was likely to be obtained using conventional RDA. Additionally, in order to increase the level of enrichment for these unique differences between tester and driver amplicons, the driver was recycled as described in Example 2.

A. Generation of Double-Stranded DNA for Amplicons. Using the procedure described herein in Materials and Methods above, Driver amplicon was prepared using total nucleic acids from 50 µl of a human plasma pool, obtained by combining equal volumes of plasma from five normal donors. Each of the donors previously had been shown by PCR and immunoassay to be hepatitis A, B, C, D, E, and GBV-A, -B and -C negative. Tester amplicon was prepared from plasma total nucleic acids in one of two manners. First, nucleic acids were extracted from 50 µl of human plasma obtained from patient LG, an individual shown by RT-PCR to contain HCV RNA at a concentration of approximately 1×10$^7$ genomes per milliliter. Second, nucleic acids were extracted from 50 µl of human plasma obtained by diluting 5 µl of LG plasma into 45 µl of the normal human plasma pool described above. This second tester amplicon was theorized to represent the equivalent of 1×10$^6$ HCV genomes per ml. The method of extraction and the procedures used for the first- and second-strand cDNA synthesis were as described in Example 2.

B. Hybridization and Selective Amplification of Amplicons. The methods and procedures used for the hybridization and selective amplification of the amplicons are described in Example 2 with a few exceptions. For example, though the tester and driver ratios were the same for rounds two, three and four of the subtractive hybridization reactions, the total driver utilized was 35 µg instead of 40 µg (12.5% less). To maintain the appropriate ratios, the amount of tester utilized was also decreased by 12.5% as compared to Example 2. Also, the length of hybridization was maintained at 22 hours for each of the subtractive components of the procedure.

C. Cloning of the Difference Products. It was observed that two DNA fragments from the third round of subtraction/amplification appeared to be present in the tester, but not the driver control. These fragments were ligated into the BamHI site of pUC18 which was then used to transform competent XL-1 Blue cells, as previously described in Example 2. Thirty-six colonies of each transformation were then grown in liquid culture from which plasmid was isolated by miniprep analysis as performed in Example 2. The largest of the two fragments was approximately 475 bp when liberated from pUC18 with a combination of the restriction enzymes EcoRI and XbaI and was present in 22 out of the 36 clones analyzed. The smaller of the two fragments was approximately 275 bp in length when liberated from pUC18 with EcoRI and XbaI and was present in 18 out of the 36 clones.

D. Identification of HCV Clones and DNA Sequence Analysis. As described in Example 3, each of the 72 plasmid DNAs were blotted onto a nylon membrane, as described in Example 3, and allowed to hybridize with a $^{32}$P-labeled probe that represented the entire HCV genome. Of the 22 clones that contained the larger insert described above in Example 5(C), 16 were hybridized with the HCV probe, while two of the 18 clones that contained the smaller insert described in Example 5(C) were hybridization positive. Six of the large insert clones that were hybridization positive, as well as both of the small insert clones, were evaluated by sequence analysis as described in Example 3. BLASTN searches (Wisconsin Sequence Analysis Package, Genetics Computer Group, Madison, Wis.; default parameters (i.e., wordsize=11, match=1, mismatch=−3, gapweight=10, lengthweight=1)) demonstrated that the large clones were identical to one another, and derived from bases 6469 to 6912 of HCV-1, the prototype genome (GenBank Number M62321). The two smaller clones were also identical to one another and represent bases 6912 to 7103 of the HCV-1 prototype genome. It was concluded from this analysis that by sufficiently reducing the complexity of two non-paired samples, and using a pooled sample as driver, amplicons could be prepared that were essentially identical for subtractive hybridization purposes. In this manner, sequences that represented authentic differences between the two nucleic acid sources may be isolated.

Example 7
Immunoisolation of a cDNA Clone Encoding an Antigenic Region of a Novel Infectious Agent The purpose of these experiments was two-fold: (i) to determine whether RDA-derived amplicons encoding immunoreactive protein domains (epitopes) of the infectious agent, when cloned into a suitable vector to generate an expression library, could be isolated by using immunoscreening and (ii) to determine whether RDA actually enriched for these sequences in successive rounds of the procedure. To test the above, the amplicons previously produced from each of the four rounds of RDA, and the unsubtracted tester amplicons, as described in Example 2, were cloned into λgt11. The resulting libraries were then immunoscreened using convalescent serum from chimp CH427 in an attempt to isolate immunoreactive epitopes encoded by HCV.

It was determined that, in order to construct a representative expression library in λgt11, RDA-derived amplicons must be represented in the library in each of the three forward reading frames. In addition, because the amplicons are restriction endonuclease digested with the enzyme Sau3aI, and because the cloning site in λgt11 only accepts EcoRI-digested DNA fragments, the amplicons required the ligation of linker/adapters that would allow expression in each of the three forward reading frames and provide an EcoRI restriction endonuclease recognition site. The linker/adapters shown in Table 2 were designed such that, when annealed together to form a double-stranded adapter, they possessed a Sau3AI-compatible 5'-overhang (5'-GATC . . . ) and an EcoRI restriction endonuclease recognition site.

TABLE 2

| Reading Frame | Name/<br>Sequence ID NO: | Sequence |
| --- | --- | --- |
| Frame 1 | BE1F/<br>SEQUENCE ID NO:13 | 5'-P-GATCCGAATTC-3' |
|  | Be1F/<br>SEQUENCE ID NO:14 | 5'-P-GAATTCG-3' |
| Frame 2 | BE2F/<br>SEQUENCE ID NO:15 | 5'-P-GATCCGGAATTC-3' |
|  | BE2R/<br>SEQUENCE ID NO: 16 | 5'-P-GAATTCGG-3' |
| Frame 3 | Be3F/<br>SEQUENCE ID NO: 17 | 5'-P-GATCGCGGAATTC-3' |
|  | BE3R/<br>SEQUENCE ID NO:18 | 5'-P-GAATTCCGC-3' |

The three sets of adapters (BE1F/R, BE2F/R, BE3F/R) were ligated to the amplicons in three separate reactions. The linker-adapted amplicons were purified away from excess linkers and then ligated to λgt11 arms, thereby generating three separate libraries, each representing one of the three possible forward (sense) reading frames. Equal numbers of recombinant phage from each of the libraries were combined to prepare the final library.

A. cDNA Library Construction

1. Preparation of the linker/adapters: 100 μM stock solutions (in water) were prepared for each of the six synthetic single-stranded oligos shown in Table 2. Twenty μl of the corresponding forward and reverse primer pair were mixed and heated for 10 min at 65° C. The tubes were then transferred to 37° C. for 10 min and then allowed to cool at room temperature (20–23° C.) for 10 min before use.

2. Preparation of amplicons: Amplicons from each of four rounds of RDA were purified to remove residual RDA-adapters that may have been present following Sau3AI digestion, phenol:chloroform extraction and ethanol precipitation. 500 ng of tester, D/T-1, D/T-2, D/T-3, D/T-4 amplicons were purified using the GeneClean kit (Bio-101, San Diego, Calif.) following the manufacturer's instructions. Since double-stranded DNA fragments less than about 200 bp in length do not bind efficiently to the glass milk resin in the kit, any residual RDA-adapters present in the amplicons should be removed. The DNA was eluted from the glass milk resin in 300 μl of water. Each sample was divided into three equal portions (100 μl) and precipitated with sodium acetate and 100% ethanol using standard methods. The yield at this stage was assumed to be nearly 100% so that each tube now contained about 166 ng of DNA.

3. Ligation of the three reading frame linker/adapters: Each of the purified RDA amplicons (166 ng) were ligated to each of the three reading frame adapters; thus, 15 separate reactions were prepared. The precipitated DNA was suspended in 2.5 μl water, and the following components were then added: 1 μl of 10×ligase buffer (200 mM Tris-HCl pH 7.6, 50 mM MgCl$_2$) 0.5 μl of 100 mM DTT, 0.5 μl of 10 mM ATP, 0.5 μl of T4 DNA ligase (2–3 Weiss units), 5 μl of 100 μM annealed reading frame 1, 2, or 3 linker adapter. Final volume was 10 μl. Reactions were incubated at 4° C. for about 16 hours. Reactions were then incubated at 65° C. to inactivate the ligase. Samples were then phenol:chloroform extracted and ethanol precipitated.

4. EcoRI digestion: The dry pellet from step 4 above was resuspended in 85 μl water and then digested with the restriction endonuclease EcoRI (100 units) in a final volume of 100 μl for 3–4 hours at 37° C. Prior to ligation of the adapted amplicons to λgt11 arms, the EcoRI-fragments released during digestion had to be removed. The samples were therefore purified by the GeneClean method as described above. The DNA was eluted in 10 μl water.

5. Ligation to λgt11 arms: The linker-adapted, purified amplicons were ligated to λgt11 arms using the λgt11 EcoRI-CIAP-treated vector kit (Stratagene, San Diego, Calif.) as directed by the manufacturer, in a final volume of 15 μl. Ligation reactions were incubated at 16° C. for about 16 hours. A negative control ligation, in which no insert was included in the reaction mix and a positive control reaction that included an insert provided by the manufacturer, were also performed.

6. Packaging and titration of the libraries: The recombinant phage were packaged into lambda phage using the GigaPack III Gold packaging extract (Stratagene, San Diego, Calif.) as directed by the manufacturer. Four microliters (4 μl) of each ligation was used for packaging. The resulting libraries (0.5 ml) were titered using E. coli Y1090r- cells (Stratagene, La Jolla, Calif.) in the presence of X-GAL and IPTG, which allowed for blue-white selection of recombinant phage using standard methods for infecting and plating. See, for example, J. Sambrook et al., supra. The titration results and volumes of each library used to make the appropriate pool are provided in Table 3. The volume of each corresponding reading frame library (e.g. from tester, D/T/-1, etc.) used to create the pooled library was calculated as follows: To yield 185,000 recombinants (i.e. phage containing inserts), one must correct for the recombination efficiency, as follows:

$$\text{volume to pool} = \frac{185{,}000 \text{ recombinants}}{\% \text{ recombinants} \times \text{plaque-forming units (pfu) titer (pfu/}\mu\text{l)}}$$

For D/T-1, the total number of clones with inserts to pool for each frame library was arbitrarily set at 171,000. Since the volume required for the tester-frame 1 library was 2.42 ml and only 0.5 ml was available, additional packaging reactions were performed to obtain 185,000 recombinants (data not shown).

TABLE 3

| LIBRARY | % RECOMBINANTS | TITER (pfu/µl) | TOTAL pfu IN LIBRARY | VOLUME FOR POOL (µl) |
|---|---|---|---|---|
| T[1]-frame 1 | 27.5 | 278 | 139000 | 500 |
| T-frame 2 | 88.8 | 812 | 406000 | 275 |
| T-frame 3 | 76.5 | 682 | 341000 | 355 |
| D/T-1-frame 1 | 92.4 | 2696 | 1346000 | 69 |
| D/T-1-frame 2 | 94.0 | 1302 | 651000 | 142 |
| D/T-1-frame 3 | 92.8 | 1482 | 741000 | 1254 |
| D/T-2-frame 1 | 96.2 | 2624 | 1312000 | 76 |
| D/T-2-frame 2 | 80.2 | 924 | 462000 | 250 |
| D/T-2-frame 3 | 82.1 | 1150 | 575000 | 196 |
| D/T-3-frame 1 | 70.6 | 1052 | 526000 | 249 |
| D/T-3-frame 2 | 71.2 | 604 | 302000 | 430 |
| D/T-3-frame 3 | 85.3 | 914 | 457000 | 237 |
| D/T-4-frame 1 | 88.7 | 2567 | 1283500 | 81 |
| D T-4-frame 2 | 85.8 | 914 | 457000 | 237 |
| D/T-4-frame 3 | 70.6 | 890 | 445000 | 295 |
| Neg control | 4.2 | 114 | 57000 | N/A[2] |
| Pos control | 97.9 | 2380 | 1190000 | N/A |

[1]T = tester
[2]N/A = not applicable

Following pooling of the frame 1, 2 and 3 libraries, the final libraries were retitered and plated as described hereinabove. These results are shown in Table 4.

TABLE 4

| LIBRARY | TITER RECOMBINANTS | TITER (pfu/µl) | VOLUME FOR POOL (µl) | TOTAL pfu IN LIBRARY |
|---|---|---|---|---|
| T-frames 1, 2, 3 | 72.9 | 273 | 1112 | 303576 |
| D/T-1-frames 1, 2, 3 | 81.1 | 1122 | 336 | 376992 |
| D/T-2-frames 1, 2, 3 | 78.6 | 814 | 522 | 424908 |
| D/T-3-frames 1, 2, 3 | 77.5 | 588 | 916 | 538608 |
| D/T-4-frames 1, 2, 3 | 85.9 | 965 | 504 | 486360 |

B. Immunoscreening of the lambda-gt11 library. The procedure used for the immunoscreening of recombinant phage was based upon the method described by Young and Davis with modifications as described below (R. A. Young and R. W. Davis, PNAS 80:1194–1198 (1983)). The primary antiserum used was convalescent serum (week 28 post inoculation) from chimpanzee CH427 (see Example 1). The antiserum was pre-adsorbed against E. coli extract prior to use in order reduce non-specific interactions of antibody with E. coli proteins, and then diluted 1:500 in Tris-buffered saline (TBS) pH 7.5 containing 1% BSA, 1% gelatin, and 3% Tween-20® ("Blocking Buffer"). 75,000 recombinant phage from each of the five libraries set forth in Table 3 were plated on a lawn of E. coli strain Y1090r- (Stratagene, La Jolla, Calif.) and grown at 37° C. for 3.5 hours. The plates were then overlayed with nylon filters that were saturated with IPTG (10 MG) and the plates incubated at 42° C. for 3.5 hours. The filters were blocked for 1 hour at 22° C. in Blocking Buffer, and then incubated in primary antiserum (1:500 dilution) at 4° C. for 16 hours. Primary antiserum was removed and saved for subsequent rounds of plaque purification. The filters washed four times in Tris-saline containing 0.1% Tween-20® (TBS-Tween). The filters were then incubated in Blocking Buffer containing alkaline-phosphatase conjugated goat anti-human IgG (0.1 (g/ml) (available from Kirkegaard and Perry, Gaithersburg, Md.) for 60 to 120 min at 22° C., washed three times with TBS-Tween, followed by one wash with TBS. Immunoreactive clones were visualized using the BCIP/NBT Color Development Kit (Bio-Rad Laboratories, Hercules, Calif., USA) as directed by the manufacturer.

The immunoreactive clones were isolated from the original plates and then subjected to a second round of immunoscreening using the methods described above. The inserts of those clones which remained immunoreactive following the second round of immunoscreening were isolated by PCR amplification of the insert using λgt11 forward and reverse primers. PCR products were separated by electrophoresis through a 2% agarose gel, and then excised and purified using the QIAEX Gel Extraction Kit (Qiagen, Chatsworth, Calif.). Purified PCR products were sequenced directly on an ABI Model 373 DNA Sequencer using the ABI Sequencing Ready Reaction Kit (Perkin-Elmer, Norwalk, Conn.) and λgt11 forward and reverse primers. The number of clones whose sequence was shown to be derived from that of the HCV strain infecting the chimp CH427 is shown in Table 5.

TABLE 5

| LIBRARY | NO. PRIMARY PICKS | NO. SECONDARY PICKS | NO. WITH HCV-DERIVED SEQ/ NO. SEQUENCE |
|---|---|---|---|
| Tester | 11 | 1 | 0/1 |
| D/T-1 | 23 | 7 | 6/6 |
| D/T-2 | 20 | 1 | 0/1 |
| D/T-3 | 61 | 31 | 22/24 |
| D/T-4 | 44 | 9 | 3/4 |

Of the 36 clones that were sequenced, analysis revealed that they all contained sequence identical to a segment of the NS5 gene from positions 6680 to 6867 of the CH427-HCV genome (GenBank accession number AF290978). It is notable that Sau3AI restriction fragment endonuclease sites are found at these two flanking positions, and that this same fragment was identified in the sequence analysis of the D/T-4 subtraction products (see Example 3). In addition, from the data shown in Table 5, it is clear that the RDA procedure enriched for this fragment in that it was represented at a higher copy number in the library from the third round of selective amplification/subtraction (D/T-3) as compared to the first or second round derived libraries. Unfortunately, it was not possible to accurately determine the fold enrichment achieved for this fragment, as no HCV-derived immunoreactive clones were obtained from the original tester amplicons. However, the feasibility of producing expression libraries in λgt11 from RDA-derived amplicons was established. It was also established that one can isolate sequences encoding epitopes derived from an infectious agent from such an expression library.

Example 8
Determination of the Degree of Enrichment of Tester-specific Sequences Achieved by Modified-RDA In order to accurately determine the degree of enrichment obtained for tester-specific sequences, the libraries prepared in λgt11 (see Example 7) were screened by southern hybridization with three cDNA probes that encompassed the entire HCV-colonel genome, as follows.

The λgt11 libraries prepared from each of the amplicons obtained for each round of modified RDA (see Table 4) were used to infect E. coli cells according to established, well-known methods. Twenty-five thousand pfu were plated for the tester and D/T-1, D/T-2, and D/T-3 libraries. For the D/T-4 library, since a preliminary experiment revealed that the density of hybridizable plaques was so high that an accurate count was not possible, the library was replated at 200 and 1000 pfu per plate. Duplicate filter lifts were prepared from duplicate filters of each library (i.e., D/T-1, 2, 3, and 4), and the filters were hybridized using standard methods with three $^{32}$P-radiolabelled cDNAs which encompassed the entire HCV genome. Following washing of the filters at high stringency and exposure to x-ray film, the number of plaques that hybridized on the duplicate filters were counted. The results are shown in Table 6.

Figure 4:
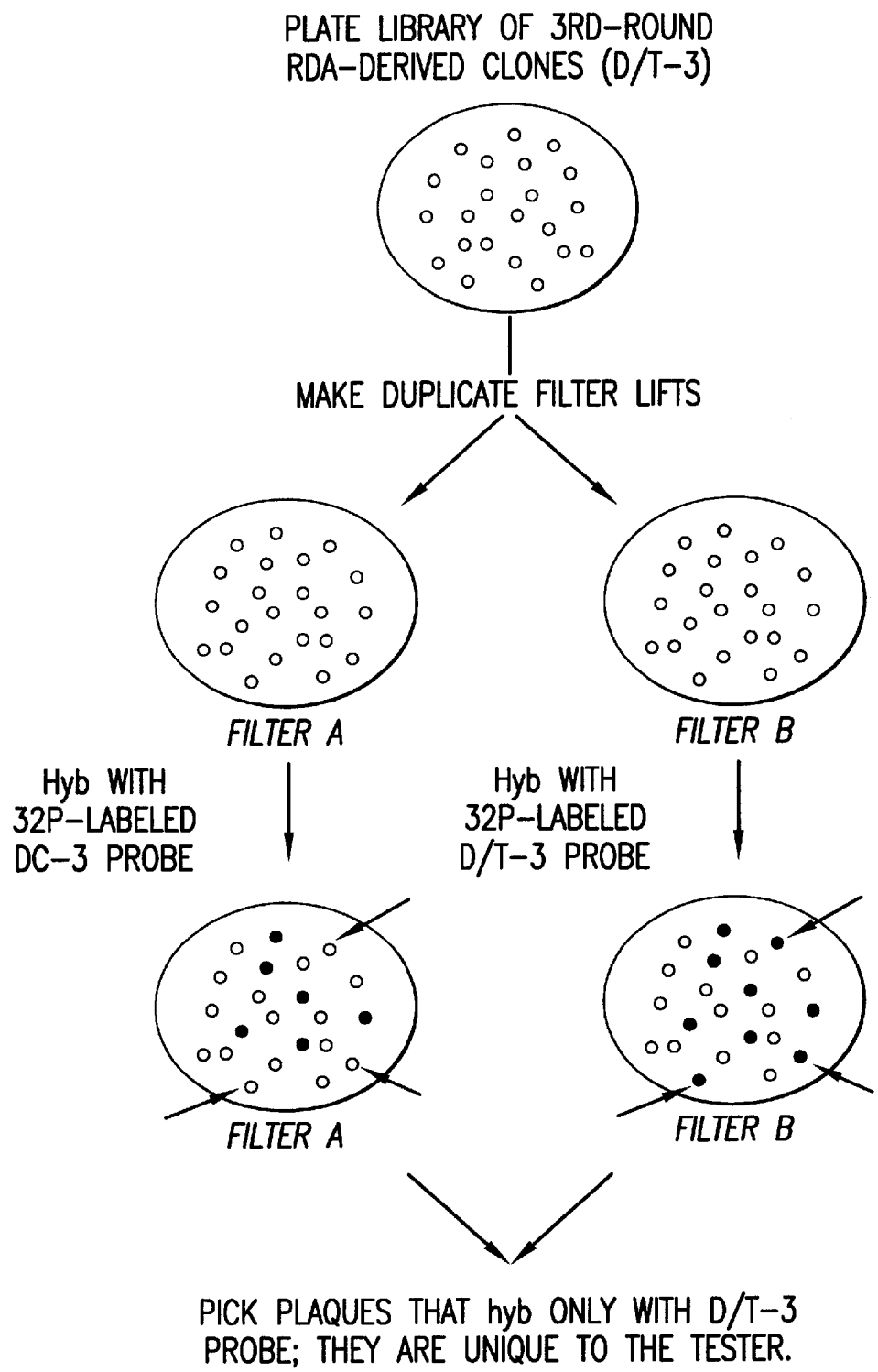
FIG. 4 presents a diagram of the steps involved in identification of target sequences by differential Hybridization as described in Example 9.

Example 9
Isolation of Tester-derived Sequences Using Differential Hybridization As demonstrated in Example 7 hereinabove, it is possible to utilize RDA followed by immunoscreening of an expression library containing tester-derived amplicons to isolate sequences derived from an infectious agent. Another method for isolating such sequences utilizes a method known as differential hybridization (see FIG. 4). (See, for example, J. Sambrook et al., "Molecular Cloning: A Laboratory Manual," $2^{nd}$ edition, Cold Spring Harbor Press, Cold Spring Harbor, N.Y. (1989).) This system involves the generation of a library from the RDA-enriched tester amplicons followed by southern hybridization of duplicate filters obtained from the same tester library plate using tester- and driver-control-derived amplicons as probes. Sequences present in the library that are found only in the tester will hybridize with the tester amplicon probe but not with the driver amplicon probe; sequences that are common to both tester and driver will hybridize with both probes. Thus, sequences that are tester-specific, and potentially derived from a novel infectious agent or possibly a gene that is upregulated during infection and/or disease, can be isolated.

The λgt11 library derived from the third round of modified RDA (D/T-3; Table 4) was utilized for differential hybridization, as follows. Five thousand plaques were plated on each of four large NZY-agar plates as described above. The phage DNA was then immobilized onto nylon filters, denatured, neutralized, UV-crosslinked and dried in an 80° C. vacuum oven for 30 minutes. Duplicate "lifts" of phage DNA were made from each plate. The filters were then hybridized with radiolabeled probe tester and driver amplicons. The probes were prepared from 25 ng of DC-3 or D/T-3 DNA, which had been digested with Sau3AI to

TABLE 6

| LIBRARY | FILTER 1 | FILTER 2 | AVERAGE | RECOMB. EFFIC.[a] | RATIO OF POS:NEG PLAQUES[b] | FOLD ENRICH.[c] |
|---|---|---|---|---|---|---|
| Tester | 33 | 33 | 33 | 0.729 | 1:552 | 1 |
| D/T-1 | 86 | 76 | 91 | 0.811 | 1:223 | 2.4 |
| D/T-2 | 598 | 632 | 615 | 0.610 | 1:25 | 22.1 |
| D/T-3 | 1192 | 1312 | 1252 | 0.775 | 1:15 | 36.8 |
| D/T-4 | 68/200 | 388/1000 | 36% | 0.854 | 1:2 | 276 |

[a]Recomb. Effic. = Recombination Efficiency. The recombination efficiency of the library was determined by plating a portion of the library in the presence of IPTG and XGAL, and then determining the number of recombinant (white) plaques and non-recombinant (blue) plagues. The efficiency is the number of white plaques obtained divided by the total number plated.
[b]Calculation of the ratio of hybridization positive to hybridization negative plagues was performed by dividing the average number of hybridization positive plagues by the number of actual recombinant plagues on the plate; i.e. 25,000 (the number of plagues plated) times the recombination efficiency of the library.
[c]Fold Enrich. = Fold enrichment. Calculation of the fold enrichment was performed by dividing the ratio of positive:negative plagues obtained for each library into that obtained for the tester library.

The results shown in Table 6 demonstrate that the modified RDA procedure enriched for HCV-specific sequences with each successive round of amplification/subtraction. At the fourth round, HCV sequences were present in one of every three clones in the library as compared to one in every 554 clones in the tester (unenriched) library. This represents an enrichment of HCV sequences of 276-fold. Thus, these data provide quantitative evidence that the modified RDA procedure results in a very significant enrichment in tester-derived sequences.

remove linker/primer sequences followed by removal of linker/primer DNA fragments using G50 Sepharose spin columns. The probes were radiolabeled using random primers followed by removal of unincorporated $^{32}$P-dATP using standard methods. One set of duplicate filters was hybridized and washed under stringent conditions with the tester probes and the other set with the driver probe. The filters were exposed to x-ray film and the autoradiographs from duplicate filters compared. Those plaques that hybridized with the tester probe, but not the driver probe, were picked for subsequent testing. A total of 12 plaques were isolated and subjected to a second round of differential hybridization screening.

From the second round screening, a total of four plaques were shown to hybridize with the tester probe. These four plaques (clones) were isolated from the plates and the insert sequence amplified using λgt11 forward and reverse primers (Stratagene, La Jolla, Calif.). PCR products were separated by electrophoresis through a 2% agarose gel and then excised and purified using the QIAEX Gel Extraction Kit (Qiagen, Chatsworth, Calif.). Purified PCR products were sequenced directly on an ABI Model 373 DNA Sequencer (PE Applied Biosystems, Foster City, Calif.) using the ABI Sequencing Ready Reaction Kit (Perkin-Elmer) and gt11 forward and reverse primers. Analysis of the resulting sequence revealed that all four clones possessed insert DNA sequences corresponding to a 437 base pair Sau3AI fragment of HCV-CH427 (from nucleotides 3514–3951). Thus, via differential hybridization of a modified-RDA enriched λgt11 library, a clone derived from HCV was isolated.

Example 10
Isolation of a Novel Virus by Subtractive Hybridization of Non-Paired Samples Using SPAD-RDA The utility of the SPAD-RDA procedure using non-paired samples was demonstrated in Example 6. This strategy was applied to a sample derived from a chimpanzee (CH19) infected with HCV but also suspected of harboring an additional unidentified virus(es). Previously, serum from a human donor containing virus-like particles was serially passed through 6 chimpanzees. A plasma pool of these chimpanzees was inoculated into CH19, resulting in acute resolving hepatitis.

Generation of Double-Stranded DNA for Amplicons: Using the procedure described herein in "Materials and Methods" above, driver amplicon was prepared using total nucleic acids from 100 μl of a plasma pool, obtained by combining equal volumes of plasma from 6 normal chimpanzees. CH19 tester amplicon was prepared from 2 pools of plasma total nucleic acids (0 to 30 days post infection and 36 to 83 days post infection). 100 μl of each tester pool was processed individually through the small scale amplicon stage, at which time equal volumes of each were combined and used to generate a single large scale tester amplicon. The method of extraction and the procedures used for the first- and second-strand cDNA synthesis were as described in Example 2.

Hybridization and Selective Amplification of Amplicons. The methods and procedures for the hybridization and selective amplification of the amplicons are described in Example 2 with the following exceptions: 1) 0.5 to 1.0 μg Sau3AI cut cDNA, representing the entire CH427 HCV genome, was added to the 40 μg of driver prior to each round of subtraction. This was done to reduce the chance that HCV, known to be present in the CH19 sample, would be enriched by SPAD-RDA, and so increase the chance that other virus(es) possibly present in the sample would be detected. 2) The length of hybridization was maintained at 21 to 22 hours for each of the subtractive components of the procedure. 3) Only 3 rounds of subtraction were performed.

Cloning of the Difference Products. Multiple DNA fragments from the 3$^{rd}$ round of subtraction/amplification appeared to be present in the tester, but not the driver control. These fragments were ligated into the pT7Blue cloning vector, which was then used to transform competent XL-1 Blue cells as described in Example 2. Twelve to 18 colonies of each transformation (72 total) were then grown in liquid culture from which plasmid was isolated, followed by miniprep analysis as in Example 2. Insert size ranged from about 350 base pairs up to 900 base pairs.

Identification of HCV Clones and DNA Sequence Analysis: As described in Example 3, 65 of the 72 plasmid DNAs were evaluated by sequence analysis. These sequences fell into 13 consensus groups. BLASTN searches (Wisconsin Sequence Analysis Package, Genetics Computer Group, Madison, Wis.; default parameters (i.e., wordsize=11, match=1, mismatch=−3, gapweight=10, lengthweight=1)) demonstrated that 7 of the consensus groups were homologous to the GB virus family, in particular GBV-C, while the other 6 consensus groups were homologous to non-viral sequences or were not found in the data base. Over 80% (54 of 65) of the clones contained sequence from the new virus, while no HCV sequences were observed. It can be concluded from this analysis that SPAD-RDA of two non-paired samples can be successfully applied to isolation of virus(s) of unknown sequence even if a known virus is present in the tester.

Example 11
Subtractive Hybridization of Paired or Non-Paired Samples Using Reduced Complexity Amplicons and a Single Hybridization Reaction as the Source for Both the Recycled Driver Control and the Target-Enriched Fraction In the preceding examples, the advantages of a recycled driver control over the single driver of the traditional RDA method were demonstrated. However, this requires that a driver control subtraction be performed in parallel with the driver/tester subtraction. Due to their separate nature, differences that arise in one subtraction, but not the other, may result in loss of the desired "paired" aspect of the products. Such differences can occur randomly or as a consequence of sequence variability between non-paired driver and tester samples. With each round of subtraction, the number and the severity of such differences will likely increase, leading to reduced driver efficiency and isolation of sequences not unique to tester (a common occurrence). It should prove beneficial to develop a method wherein the generation of the driver control and the driver/tester subtraction products are linked in such a manner as to minimize these differences. The following example is proposed as a method for accomplishing this goal.

Figure 5:
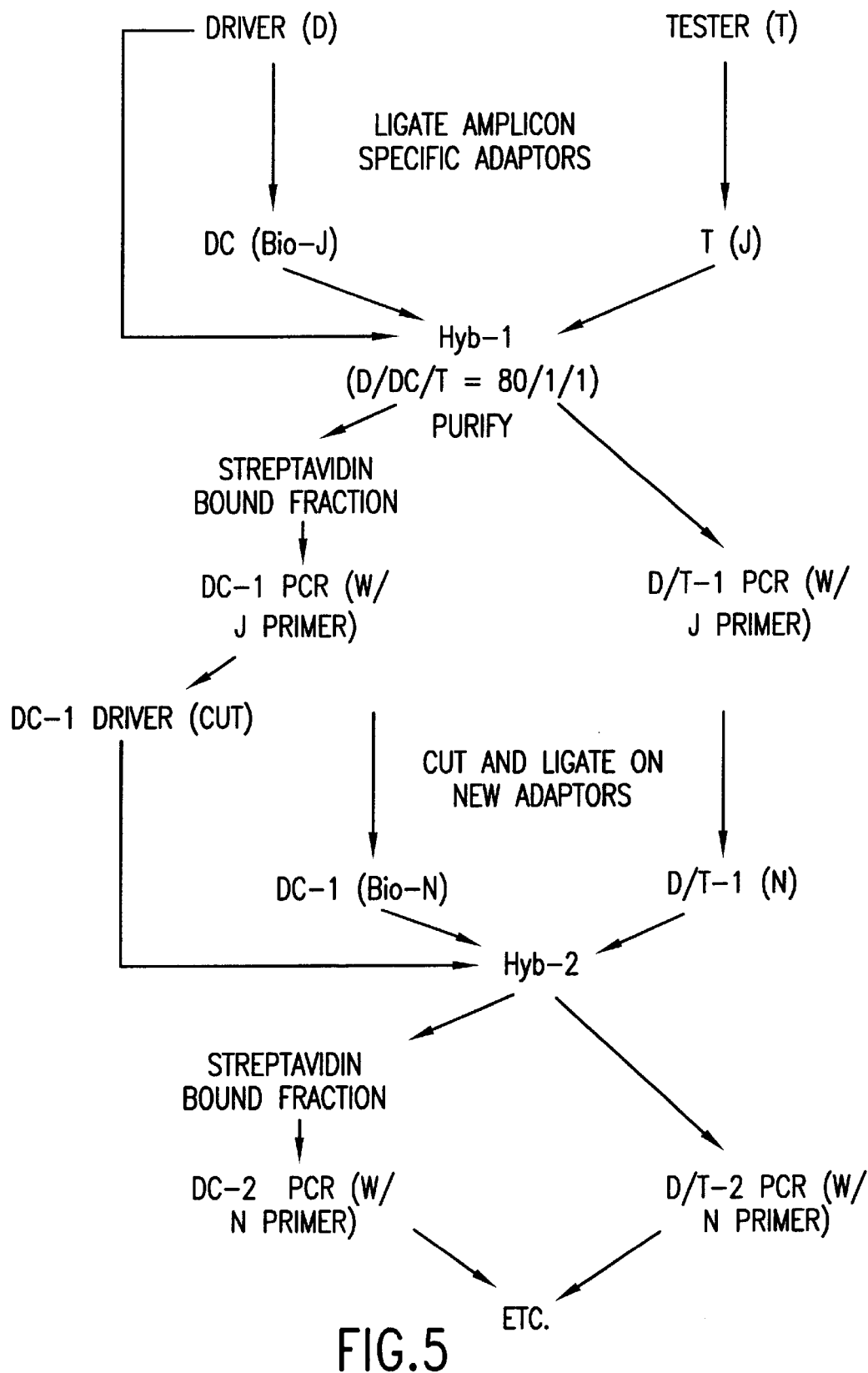
FIG. 5 presents a diagram of the steps involved in the proposed "single hybridization" RDA modification.

A. Generation of Double-Stranded DNA for Amplicons. Double-stranded DNA for D and T are prepared as described hereinabove in Example 2 (part A).
B. Generation of Amplicons. D and T amplicons would be prepared as described hereinabove in Example 2 (part B).
C. Hybridization and Selective Amplification of Amplicons. The desired number of rounds of subtractive hybridization are performed as described above in Example 2 (part C), except as described below and in FIG. 5.

The oligonucleotide that is ligated onto the DC contains a 5-prime biotin label (e.g. 5'-Bio J-Bam 24, SEQUENCE ID NO: 5). The same oligonucleotide, without biotin (e.g. J-Bam 24, SEQUENCE ID NO: 5), is ligated onto the tester. Next, a single hybridization mixture (Hyb-1) is made, comprised of the D amplicon (40 μg), plus DC (0.5 μg) and T (0.5 μg) amplicons ligated to the J-Bam adaptor set with or without the 5-prime biotin label respectively (80/1/1 ratio). Following the 67° C. hybridization and dilution with TE buffer, 50 μl (20 μg) of the hybridization reaction are purified (e.g., with the QIAquick® PCR Purification Kit, QIAGEN, Chatwworth, Calif.) according to manufacturer's instructions, final volume 60 μl) so as to eliminate non-ligated oligonucleotides. This purification is included to prevent any residual 5'-Bio J-Bam 24 (SEQUENCE ID NO: 5) from interfering with the subsequent streptavidin purification step.

A portion (12 μl 4 μg DNA) of the purified hybridization reaction is set aside for amplification of the target-enriched fraction. Another portion is reserved for purification of the DC fraction (i.e., biotin-containing molecules) using streptavidin coated paramagnetic particles (SA-PMP's, e.g., MagneSphere$^R$ from Promega) as described by D. J. Lavery et al., *Proc. Natl. Aca. Sci. USA* 94:6831–6836 (1997), and modified. In particular, the SA-PMP's (80 μl) is resuspended and washed 3 times at room temperature (RT) with 300 μl 1 M TENT buffer (10 mM Tris, 1 mM EDTA, 0.1% Triton X-100, 1 M NaCl, pH 8.0) containing 20 ng/μl synthetic poly A DNA, added to help prevent non-specific binding of the hybridization products to the SA-PMP's. Washed SA-PMP's is resuspended in 200 μl of 1 M TENT/poly A buffer. The remaining 48 μl (16 μg) of the purified hybridization reaction is adjusted to 0.1 M NaCl by the addition of 1 μl of a 5 M stock, and combined with the washed SA-PMPs. Binding of biotin-labeled hybridization products to the SA-PMPs is allowed to proceed from 30 minutes up to 2 hours at RT with occasional mixing. Non-bound DNA is eliminated by washing 3 times at RT with 300 μl 1 M TENT buffer, followed by 2 high stringency washes with 300 μl 50 mM TENT buffer (10 mM Tris, 1 mM EDTA, 0.1% Triton X-100, 50 mM NaCl, pH 8.0) at 60° C. Finally, the SA-PMP's would be washed 2 times with 300 μl 10 mM Tris (pH 8.5) at RT and resuspended in a final volume of 48 μl of the same.

All subsequent steps of PCR amplification and nuclease digestion are performed as described in Example 2 (part C) except that starting templates for DC-1 and D/T-1 PCR are 12 μl SA-PMP bound DNA or 12 μl of the purified hybridization reaction DNA, respectively.

D. Subsequent Hybridization/Amplification Steps and Cloning/Analysis of the Difference Products Additional rounds of subtraction are performed as described in Example 2 (part D) with the exceptions noted in Example 10 (part C). Cloning and analysis of sequences of interest is performed as described in Example 2 (part E) and in Example 3, respectively.

The above examples demonstrate the utility of the SPAD-RDA method of the present invention and the advantages it has over the conventional RDA method. This improvement to known modified methods of Simons et al. and Hubank et al. also is apparent (citations above). By using the SPAD-RDA method of the present invention, amplicon complexity can be reduced while simultaneously achieving a more detailed sampling of all sequences. Further, driver composition parallels that which is optimal at any particular stage, and an example is provided that directly links driver composition to that of the subtracted tester, even with a non-paired driver. Finally, visual comparison can be used to identify those subtraction products of interest.

Beyond visual identification, recombinant libraries prepared from the SPAD-RDA products can be analyzed by immunoscreening and by differential hybridization to identify tester-unique sequences. These all combine to allow the identification and isolation of many target sequences that otherwise would be difficult or impossible to isolate, such as those contained within a complex genomic background and/or present at a low copy number.

What is claimed is:

1. A method for performing subtractive hybridization using a tester sample and a driver sample to determine the presence of a nucleic acid sequence difference in the tester sample comprising:

(a) separately isolating total nucleic acid from the tester sample and the driver sample, and generating double-stranded cDNA or DNA from said total nucleic acid from said tester sample and said driver sample;

(b) digesting said double-stranded cDNA or DNA generated from the tester sample and the drive sample of step (a) with a restriction endonuclease in order to produce a set of restriction fragments for each sample;

(c) ligating said driver and tester restriction fragments of each set of step (b) to a first oligonucleotide adapter set, and amplifying the resulting products with selective primers such that a subset of said restriction fragments of step (b) is amplified;

(d) removing said selective primer sequences by restriction endonuclease digestion in order to produce tester and driver amplicons, ligating the 5'-ends of said driver and tester amplicons to a second oligonucleotide adapter set to form driver-control and tester, mixing the driver-control and tester separately with an excess of non-ligated driver amplicon each, denaturing said resulting mixtures, and allowing the denatured nucleic acid strands within each mixture to hybridize;

(e) filling in the 3'-ends of the reannealed driver/tester and the reannealed driver/driver control using a thermostable DNA polymerase and amplifying the resulting sequences;

(f) removing the remaining single-stranded DNA by digesting said DNA with a single-stranded DNA nuclease;

(g) amplifying double-stranded DNA remaining after nuclease digestion; and (h) cleaving the subtraction products of the driver/tester and driver/driver-control with a restriction endonuclease to remove oligonucleotide adapters, and repeating steps (c) through (h), whereas steps (c) through (h) utilize an oligonucleotide adapter set not used in any previous round, wherein one round consists of performance of steps (c) through (h), and utilize as driver, for each new round, the restriction endonuclease-cleaved product of the driver/driver-control subtraction from immediately proceeding steps (c) through (h).

2. The method of claim 1 wherein the restriction endonuclease of step (b) has a 4–6 basepair recognition site.

3. The method of claim 2 wherein said restriction endonuclease of step (b) has a 4 basepair recognition site.

4. The method of claim 3 wherein said restriction endonuclease is Sau3AI.

5. The method of claim 1 wherein said restriction enzyme of step (h) has a 4–6 basepair recognition site.

6. The method of claim 5 wherein said restriction enzyme of step (b) has a 4 basepair recognition site.

7. The method of claim 6 wherein said restriction enzyme is Sau3AI.

8. A method for visual identification of unique tester sequences comprising the steps of:

(a) separately isolating total nucleic acid from a tester sample and a driver sample, and generating double-stranded cDNA or DNA from said total nucleic acid from said tester sample and said driver sample;

(b) digesting said double-stranded cDNA or DNA generated from the tester sample and the driver sample of step (a) with a restriction endonuclease in order to produce a set of restriction fragments for each sample;

(c) ligating said driver and tester restriction fragments of step (b) to a first oligonucleotide adapter set, and amplifying the resulting products with selective primers such that a subset of said restriction fragments of step (b) is amplified;

(d) removing said selective primer sequences by restriction endonuclease digestion in order to produce tester and driver amplicons, ligating the 5'-ends of said driver and tester amplicons to a second oligonucleotide adapter set to form driver-control and tester, mixing the driver-control and tester separately with an excess of non-ligated driver amplicon each, denaturing said resulting mixtures, and allowing the denatured nucleic acid strands within each mixture to hybridize;

(e) filling in the 3'-ends of the reannealed driver/tester and reannealed driver/driver-control using a thermostable DNA polymerase and amplifying the resulting sequences;

(f) removing the remaining single-stranded DNA by digesting said DNA with a single-stranded DNA nuclease;

(g) amplifying the double-stranded DNA remaining after nuclease digestion; and (h) cleaving the subtraction products of the driver/tester and driver/driver-control with a restriction endonuclease to remove oligonucleotide adapters, repeating steps (c) through (h), wherein steps (c) through (h) utilize an oligonucleotide adapter set not used in any previous round of RNA, wherein one round consists of performance of steps (c) through (h), and utilized as driver, for each new round of RDA, the restriction endonuclease-cleaved product of the driver/driver-control subtraction from immediately preceeding steps (c) through (h);

(i) placing said driver-tester and driver-control products on a solid substrate; and (j) visually identifying driver tester bands not present in said driver-control bands.

* * * * *